United States Patent
Buckland et al.

(10) Patent No.: US 10,307,056 B2
(45) Date of Patent: Jun. 4, 2019

(54) SYSTEMS AND METHODS FOR QUANTITATIVE DOPPLER OPTICAL COHERENCE TOMOGRAPHY

(71) Applicant: Bioptigen, Inc., Morrisville, NC (US)

(72) Inventors: Eric L. Buckland, Hickory, NC (US); Bradley A. Bower, Hillsborough, NC (US); Ryan Gessner, Carrboro, NC (US)

(73) Assignee: Bioptigen, Inc., Morrisville, NC (US)

( * ) Notice: Subject to any disclaimer, the term of this patent is extended or adjusted under 35 U.S.C. 154(b) by 663 days.

(21) Appl. No.: 14/561,684

(22) Filed: Dec. 5, 2014

(65) Prior Publication Data

US 2015/0157205 A1 Jun. 11, 2015

Related U.S. Application Data

(60) Provisional application No. 61/912,159, filed on Dec. 5, 2013.

(51) Int. Cl.
  *A61B 3/10* (2006.01)
  *A61B 3/00* (2006.01)
  *A61B 3/12* (2006.01)

(52) U.S. Cl.
  CPC .......... *A61B 3/1233* (2013.01); *A61B 3/0025* (2013.01); *A61B 3/102* (2013.01)

(58) Field of Classification Search
  CPC ......... A61B 3/102; A61B 3/14; A61B 3/1025; A61B 3/1225; A61B 3/0025

(Continued)

(56) References Cited

U.S. PATENT DOCUMENTS 3,498,290 A 3/1970 Shaw et al.
3,939,707 A 2/1976 Kossoff
(Continued)

FOREIGN PATENT DOCUMENTS

WO WO 2010/138645 A2 12/2010

OTHER PUBLICATIONS

Barton et al., "Flow measurement without phase information in optical coherence tomography images," Optics Express, vol. 13, No. 14, Jul. 11, 2005, pp. 5234-5239.
(Continued)

*Primary Examiner* — Robert E. Tallman
(74) *Attorney, Agent, or Firm* — Stanek Lemon Crouse & Meeks, PA

(57) ABSTRACT

Methods of obtaining a measure of blood flow using a Fourier domain optical coherence tomography (FDOCT) system is provided. The method includes obtaining a first optical coherence tomography (OCT) survey scan of a retina of a subject using an OCT scan beam and obtaining a second OCT scan of the retina. The second OCT scan is within an area defined by the obtained first OCT scan and includes a region of retinal blood vessels emerging from and returning to an Optic Nerve Head (ONH) of the retina. An optical phase change is determined from the obtained second OCT scan, the optical phase change being associated with blood flow in a retinal blood vessel in the region of the second OCT scan. An angle of the retinal blood vessel associated with the optical phase change is determined, the angle being measured relative to a direction of transmission of the OCT scan beam. A quantitative measure of vessel blood flow is computed using the optical phase change and the vessel angle relative to the direction of the OCT scan beam.

22 Claims, 17 Drawing Sheets

(58) Field of Classification Search
USPC .................................. 351/206, 246, 221, 210
See application file for complete search history.

(56) References Cited

U.S. PATENT DOCUMENTS

| | | | |
|---|---|---|---|
| 4,257,278 | A | 3/1981 | Papadofrangakis et al. |
| 4,265,126 | A | 5/1981 | Papadofrangakis et al. |
| 4,807,636 | A | 2/1989 | Skidmore et al. |
| 5,150,421 | A | 9/1992 | Morishita et al. |
| 5,204,627 | A | 4/1993 | Mistretta et al. |
| 5,226,113 | A | 7/1993 | Cline et al. |
| 5,233,299 | A | 8/1993 | Souza et al. |
| 5,297,551 | A | 3/1994 | Margosian et al. |
| 5,368,033 | A | 11/1994 | Moshfeghi |
| 5,390,677 | A | 2/1995 | Ferrera et al. |
| 5,501,226 | A | 3/1996 | Petersen et al. |
| 5,549,114 | A | 8/1996 | Petersen et al. |
| 5,555,886 | A | 9/1996 | Weng et al. |
| 5,623,930 | A | 4/1997 | Wright et al. |
| 5,760,781 | A | 6/1998 | Kaufman et al. |
| 5,769,079 | A | 6/1998 | Hossack |
| 6,006,128 | A | 12/1999 | Izatt et al. |
| 6,102,864 | A | 8/2000 | Hatfield et al. |
| 6,436,049 | B1 | 8/2002 | Kamiyama et al. |
| 6,468,218 | B1 | 10/2002 | Chen et al. |
| 6,519,354 | B1 | 2/2003 | Oshio |
| 6,735,463 | B2 | 5/2004 | Izatt et al. |
| 6,780,155 | B2 | 8/2004 | Li |
| 6,904,163 | B1 | 6/2005 | Fujimura et al. |
| 7,004,906 | B1 | 2/2006 | Guracar et al. |
| 7,006,232 | B2 | 2/2006 | Rollins et al. |
| 7,020,318 | B2 | 3/2006 | Oshio et al. |
| 7,113,817 | B1 | 9/2006 | Winchester, Jr. et al. |
| 7,170,517 | B2 | 1/2007 | Raman et al. |
| 7,301,644 | B2 | 11/2007 | Knighton et al. |
| 7,359,062 | B2 | 4/2008 | Chen et al. |
| 7,505,142 | B2 | 3/2009 | Knighton et al. |
| 7,554,669 | B2 | 6/2009 | Buckland et al. |
| 7,591,787 | B2 | 9/2009 | Tortoli |
| 7,744,221 | B2 | 6/2010 | Wei et al. |
| 7,869,663 | B2 | 1/2011 | Buckland et al. |
| 7,995,814 | B2 | 8/2011 | Fingler et al. |
| 8,244,334 | B2 | 8/2012 | Huang et al. |
| 8,369,594 | B2 | 2/2013 | Fingler et al. |
| 8,401,257 | B2 | 3/2013 | Izatt et al. |
| 8,442,356 | B2 | 5/2013 | Buckland et al. |
| 8,687,856 | B2 | 4/2014 | Bower et al. |
| 8,744,159 | B2 | 6/2014 | Bower et al. |
| 8,787,623 | B2 | 7/2014 | Bower et al. |
| 2005/0171438 | A1 | 8/2005 | Chen et al. |
| 2007/0025642 | A1 | 2/2007 | Buckland et al. |
| 2007/0115481 | A1 | 5/2007 | Toth et al. |
| 2009/0005691 | A1 | 1/2009 | Huang et al. |
| 2010/0166293 | A1* | 7/2010 | Sugita .................... A61B 3/102 382/154 |
| 2011/0043661 | A1* | 2/2011 | Podoleanu ............. A61B 3/102 348/239 |
| 2011/0096291 | A1* | 4/2011 | Buckland ............... A61B 3/102 351/206 |
| 2011/0160576 | A1 | 6/2011 | Bower et al. |
| 2012/0194783 | A1 | 8/2012 | Wei et al. |
| 2012/0275677 | A1 | 11/2012 | Bower et al. |
| 2012/0307014 | A1* | 12/2012 | Wang .................... A61B 3/102 348/46 |
| 2013/0039557 | A1* | 2/2013 | Wei .................... G06K 9/00214 382/131 |

OTHER PUBLICATIONS

Baumann et al., "Total retinal blood flow measurement with ultra-high speed swept source/Fourier domain OCT," Biomedical Optics Express, vol. 2, No. 6, Jun. 1, 2011, pp. 1539-1552.

Bruckner, Stefan, "Introduction to Scientific Visualization," Simon Fraser University / Vienna University of Technology, PowerPoint presentation, 17 pages, Printed from the Internet Feb. 14, 2010, https://www.cs.ubc.ca/~tmm/courses/533-09/slides/scivis-6up.pdf.

Chen et al., "Optical Doppler tomographic imaging of fluid flow velocity in highly scattering media," Optics Letters, vol. 22, No. 1, Jan. 1, 1997, pp. 64-66.

Dave et al., "Doppler-angle measurement in highly scattering media," Optics Letters, vol. 25, No. 20, Oct. 15, 2000, pp. 1523-1525.

DeLoid et al. "A Metric for Quantitative Analysis of Vascular Tortuosity," Microsc Microanal 11 (Suppl 2), 2005, pp. 1022-1023.

Gelman et al., "Diagnosis of Plus Disease in Retinopathy of Prematurity Using Retinal Image multiScale Analysis," Investigative Ophthalmology & Visual Science, Dec. 2005, vol. 46, No. 12, pp. 4734-4738.

Heidrich et al, "Interactive Maximum Projection vol. Rendering," Sixth IEEE Visualization 1995, Abstract, Printed from the Internet Feb. 14, 2010, http://www.computer.org/portal/web/cdle/doi/10.1109/VISUAL.1995.48-790.

Hylton, Nola M., "Angiographic display method for flow-enhanced MRI," Abstract, Jun. 1992, Printed from the Internet Feb. 14, 2010, http://adsabs.harvard.edu/abs/1992SPIE.1652, 2 pages.

Izatt et al., "In vivo bidirectional color Doppler flow imaging of picoliter blood volumes using optical coherence tomography," Optics Letters, vol. 22, No. 18, Sep. 15, 1997, pp. 1439-1441.

Johnson et al, "A Method for Estimating the Sub-wavelength Sway of a Sonar Towfish," IEEE Journal of Oceanic Engineering, vol. 20, No. 4, Oct. 1995, pp. 258-267.

Johnson et al., "Robust measures of three-dimensional vascular tortuosity based on the minimum curvature of approximating polynomial spline fits to the vessel mid-line," Elsevier Science Journal, Medical Engineering & Physics, vol. 29, Issue 6, Jul. 2007, 38 pages.

Kaufman et al., "Real-Time Volume Rendering," to appear in the International Journal of Imaging Systems and Technology, special issue on 3D Imaging, 2000, 9 pages.

Kim et al., A New Doppler Method for Quantification of Volumetric Flow: In Vivo Validation Using Color Doppler, JACC, vol. 27, No. 1, Jan. 1996, pp. 182-192.

Leitgeb et al, "Real-time measurement of in vitro flow by Fourier-domain color Doppler optical coherence tomography," Optics Letters, vol. 29, No. 2, Jan. 15, 2004, pp. 171-173.

Makita et al., "Quantitative retinal-blood flow measurement with three-dimensional vessel geometry determination using ultrahigh-resolution Doppler optical coherence angiography," Optics Letters, vol. 33, No. 8, Apr. 15, 2008, pp. 836-838.

Mariampillai et al., "Speckle variance detection of microvasculature using swept-source optical coherence tomography," Optics Letters, vol. 33, No. 13, Jul. 1, 2008, pp. 1530-1532.

Michaely et al., Intensity based quantification of fast retinal blood flow in 3D via high resolution resonant Doppler spectral OCT, Proc. of SPIE-OSA Biomedical Optics, SPIE vol. 6627, 2007, pp. 66270J-1 to 66270J-10.

U.S. Appl. No. 12/101,006, filed Apr. 10, 2008.

Pedersen et al., "Phase-referenced Doppler optical coherence tomography in scattering media," Optics Letters, vol. 30, No. 16, Aug. 15, 2005, pp. 2125-2127.

Piao et al., "Direct bidirectional angle-insensitive imaging of the flow signal intensity of Doppler optical coherence tomography," Applied Optics, vol. 44, No. 3, Jan. 20, 2005, pp. 348-357.

Ren et al., "Imaging and quantifying transverse flow velocity with the Doppler bandwidth in a phase-resolved functional optical coherence tomography," Optics Letters, vol. 27, No. 6, Mar. 15, 2002, pp. 409-411.

Srinivasan et al., "Quantitative cerebral blood flow with Optical Coherence Tomography," Optics Express, vol. 18, No. 3, Feb. 1, 2010, pp. 2477-2494.

Tokayer, Jason, "A Review of Doppler OCT: From Past to Present," Presentation for Dr. Fujimoto, MIT—Jul. 9, 2009, 30 pages.

Totsuka et al., "Frequency Domain Volume Rendering," 1993, Sony Corporation, Stanford University, pp. 271-278.

Wallace, David K., Computer-Assisted Quantification of Vascular Tortuosity in Retinopathy of Prematurity (An American Ophthalmological Society Thesis), Trans Am Ophthalmol Soc, vol. 105, 2007, pp. 594-615.

(56) References Cited

OTHER PUBLICATIONS

Wang et al., "Characterization of fluid flow velocity by optical Doppler tomography," Optics Letters, vol. 20, No. 11, Jun. 1, 1996, pp. 1337-1339.

Wang et al., "Frequency domain phase-resolved optical Doppler and Doppler variance tomography," Optics Communications, vol. 242, 2004, pp. 345-350.

Wang et al., "Pilot Study of Optical Coherence Tomography Measurement of Retinal Blood Flow in Retinal and Optic Nerve Diseases," IOVS Papers in Press, Published on Nov. 4, 2010 as Manuscript iovs.10-5985, The Association for Research in Vision and Ophthalmology, Inc., 30 pages.

Wehbe et al., "Automatic retinal blood flow calculation using spectral domain optical coherence tomography," Optics Express, vol. 15, No. 23, Nov. 12, 2007, pp. 15193-15206.

Wehbe et al., "Automatic retinal blood vessel parameter calculation in spectral domain optical coherence tomography," Proc. of SPIE, Vo. 6429, 2007, pp. 64290D-1 to 64290D-7.

White et al., "In vivo dynamic human retinal blood flow imaging using ultra-high-speed spectral domain optical Doppler tomography," Optics Express, vol. 11, No. 25, Dec. 15, 2003, pp. 3490-3497.

Yang et al., "High speed, wide velocity dynamic range Doppler optical coherence tomography (Part I): System design, signal processing, and performance," Optics Express, vol. 11, No. 7, Apr. 7, 2003, pp. 794-809.

Yang et al., "High speed, wide velocity dynamic range Doppler optical coherence tomography (Part II): Imaging in vivo cardiac dynamics of *Xenopus laevis*," Optics Express, vol. 11, No. 14, Jul. 14, 2003, pp. 1650-1658.

Yang et al., Interstitial Doppler optical coherence tomography, Optics Letters, vol. 30, No. 14, Jul. 15, 2005, pp. 1791-1793.

\* cited by examiner

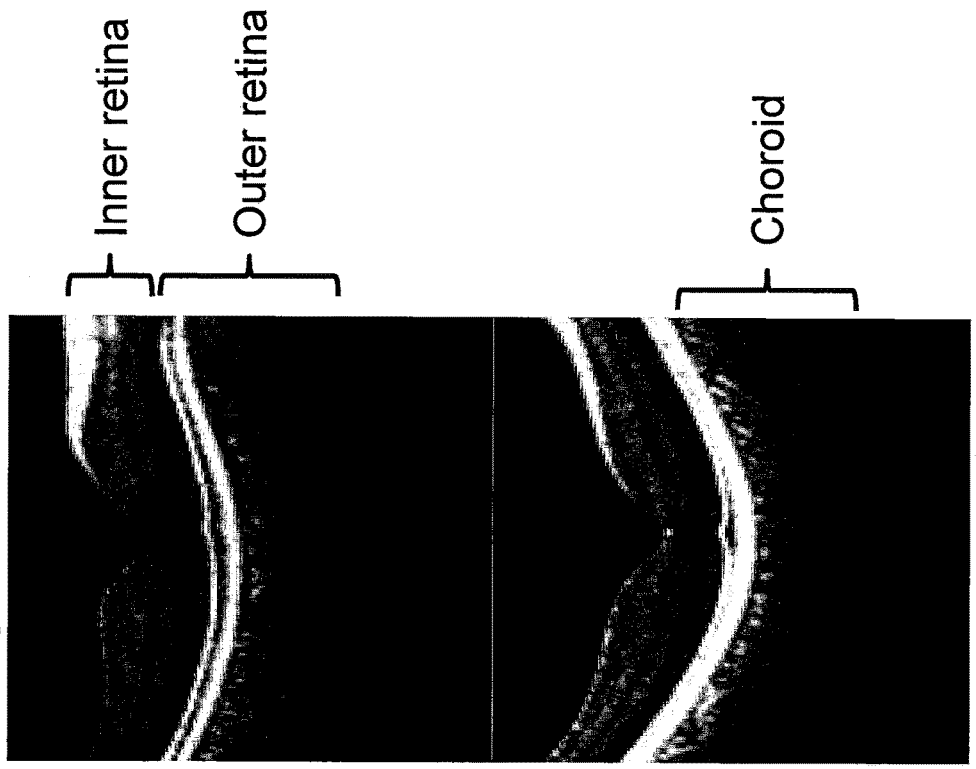
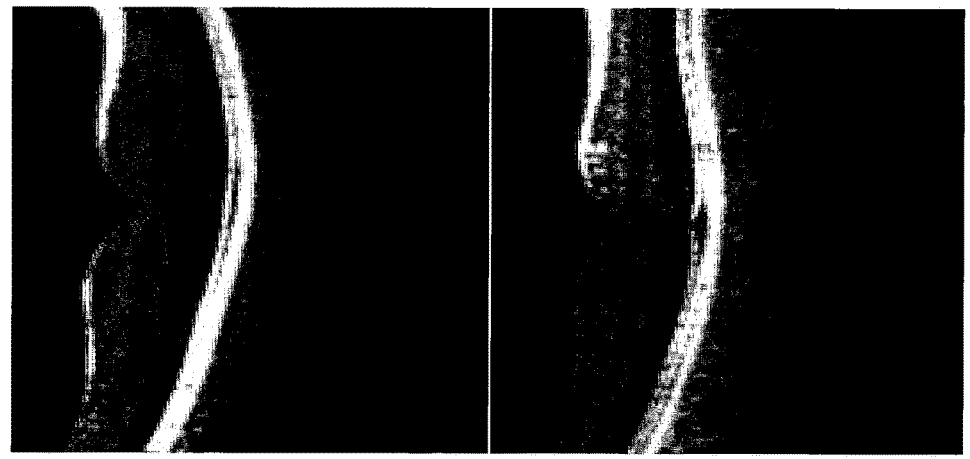

SYSTEMS AND METHODS FOR QUANTITATIVE DOPPLER OPTICAL COHERENCE TOMOGRAPHY

CLAIM OF PRIORITY

The present application claims priority from U.S. Provisional Application No. 61/912,159, filed Dec. 5, 2013, the disclosure of which is hereby incorporated herein by reference as if set forth in their entirety.

FIELD

The present inventive concept relates to imaging and, more particularly, to optical coherence tomography (OCT) and related systems, methods and computer program products.

BACKGROUND

Blood flow measurements in the eye are important to diagnose and monitor progression of diseases and treatment outcomes as a way to reduce the likelihood, or possibly, prevent blindness. The eye is a delicate and sensitive organ that can be damaged by a variety of chronic conditions as well as by acute trauma.

Improved blood flow measurement technology can help to diagnose, monitor and, therefore, possibly prevent blindness. Three of the five most common causes of blindness, macular degeneration, glaucoma, and diabetic retinopathy, are related to the flow of blood in the eye. These conditions must be diagnosed in a timely manner and the treatment must be monitored.

Optical Coherence Tomography (OCT) provides real time images of surface and subsurface structures, and is of particular clinical importance in imaging of the retina. Second generation OCT systems rely on Fourier domain techniques; interference signals are acquired in the optical frequency domain and transformed to the spatial domain. Such techniques include swept source implementations, occasionally referred to as Optical Frequency Domain Imaging (OFDI), or spectrometer-based implementations, referred to equivalently as Spectral Domain OCT or "spectral radar." A key advantage of Fourier domain techniques is image speed, and commercial speeds of 30 kHz to 100 kHz are now available, and in research labs speeds to 1 MHz (rate for single depth-resolved A-line acquisition) have been reported.

In addition to the structural imaging afforded by OCT, a number of techniques have been proposed for imaging flow, analogous to ultrasound Doppler imaging. Techniques include Color Doppler OCT appropriate for bidirectional flow imaging, and phase-variance or speckle-variance techniques for visualizing the presence of motion. Doppler OCT is discussed in, for example, in U.S. Pat. No. 6,006,128 to Izatt, the contents of which is hereby incorporated herein by reference.

In general, Doppler OCT results are derived from components of flow that co-propagate or counter-propagate with respect to the OCT imaging beam. The process of deriving a physically or physiologically relevant value, such as flow velocity or flow rate requires an assessment of additional parameters, including the angle of flow relative to the interrogating beam and the area of the lumen constraining the flow, and consideration of pulsatility of flow. Error in any of these complementary measures rapidly increases error in quantitative computation of the desired result.

Despite more than a decade of research, there has been no commercialization of a quantitative Doppler OCT system. U.S. Pat. No. 8,244,334 to Huang et al. proposes a dual circumpapillary scan for computing blood flows out of and into the optic nerve head of the eye, but this technique has not been demonstrated to have an accuracy or precision suitable for diagnostic outputs. Furthermore, the eye is served by two circulatory systems: the retinal circulatory system nourishing the inner retina; and the uveal circulatory system, nourishing the outer retina. The circumpapillary approach does not provide information on the uveal circulatory system.

SUMMARY

Some embodiments of the present inventive concept provide methods of obtaining a measure of blood flow using a Fourier domain optical coherence tomography (FDOCT) system. The method includes obtaining a first optical coherence tomography (OCT) survey scan of a retina of a subject using an OCT scan beam and obtaining a second OCT scan of the retina. The second OCT scan is within an area defined by the obtained first OCT scan and includes a region of retinal blood vessels emerging from and returning to an Optic Nerve Head (ONH) of the retina. An optical phase change is determined from the obtained second OCT scan, the optical phase change being associated with blood flow in a retinal blood vessel in the region of the second OCT scan. An angle of the retinal blood vessel associated with the optical phase change is determined, the angle being measured relative to a direction of transmission of the OCT scan beam. A quantitative measure of vessel blood flow is computed using the optical phase change and the vessel angle relative to the direction of the OCT scan beam.

In further embodiments of the present inventive concept, the method may further include obtaining a third OCT scan of the retina, the third scan being within the area defined by the obtained first OCT scan and including a region of uveal blood vessels; determining a second optical phase change from the obtained third OCT scan associated with blood flow in a uveal vessel in the region of the third OCT scan; determining a second angle of a vessel associated with the second optical phase change from the obtained third OCT scan, the second angle measured relative to the direction of transmission of the OCT scan beam; and computing a quantitative measure of vessel blood flow using the second optical phase change and the second vessel angle relative to the direction of the OCT scan beam.

In still further embodiments, the method may further include displaying at least one of a measure of retinal blood flow and a measure of uveal blood flow.

In some embodiments, the uveal region may be a choroidal region.

In further embodiments, the FDOCT system may be one of a spectral domain OCT system and a swept source OCT system.

In still further embodiments, the first OCT survey scan may be an en face image against which subsequent scans are registered for positional reference.

Some embodiments of the present inventive concept provide methods for computing clinical values using an FDOCT system. The method including obtaining an OCT scan of a retina of a subject; measuring flow in a retinal blood vessel; measuring flow in a uveal blood vessel; and computing a functional relationship between the measured retinal and uveal blood flows.

Further embodiments of the present inventive concept provided methods for computing clinical values using an FDOCT system. The method includes obtaining a first OCT scan of a retina of a subject; measuring flow in a retinal blood vessel; measuring flow in a uveal blood vessel; obtaining a second OCT scan of the retina; measuring flow in a second retinal blood vessel; measuring flow in the uveal blood vessel; and computing a functional relationship between the measured retinal blood flows in the first and second OCT scans.

In still further embodiments, the method may further include computing a functional relationship between the measured uveal blood flows in the first and second OCT scans.

In some embodiments, the method may further include computing a functional relationship between the retinal blood flows and the uveal blood flows obtained in the first and second OCT scans.

In further embodiments, where the functional relationships may represent changes in retinal and uveal blood flows over time and where the changes may result from at least one of disease progression, influence of stimulus and or application of therapy.

Still further embodiments of the present inventive concept provide an FDOCT imaging system comprising a source of broadband optical radiation; imaging optics to direct a scanning beam of the optical radiation to a retina of a subject; and a processor configured to scan the beam of optical radiation in one or more defined patterns and derive separate measures of blood flow in the retinal and the uveal circulatory systems.

BRIEF DESCRIPTION OF THE FIGURES

FIGS. 2A through 2D are images illustrating retinas of various ethnic groups.

BRIEF DESCRIPTION OF EMBODIMENTS

Figure 1A:
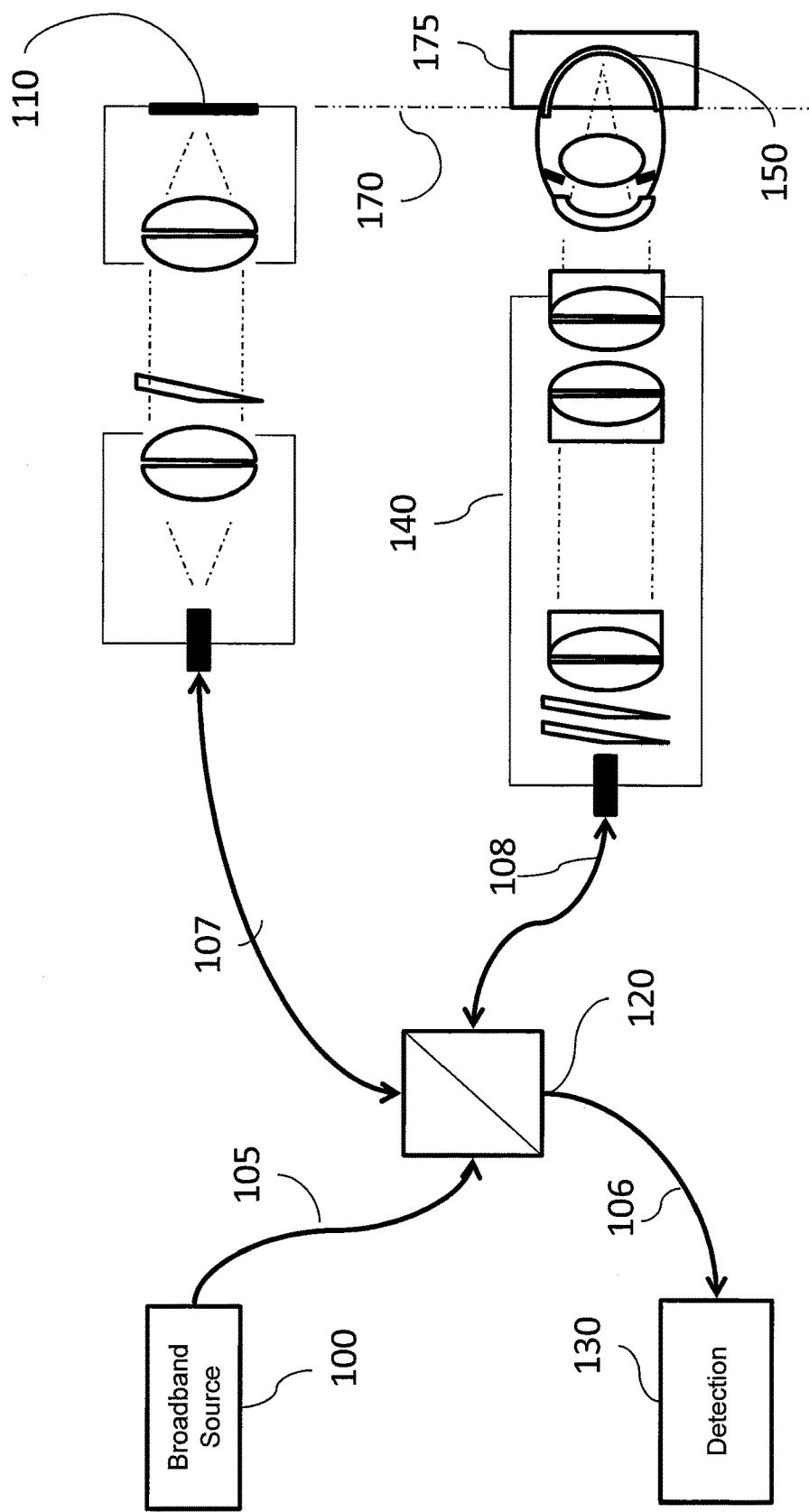
FIG. 1A is a block diagram illustrating a Fourier domain Optical Coherence Tomography (FDOCT) system.

The present inventive concept will be described more fully hereinafter with reference to the accompanying figures, in which embodiments of the inventive concept are shown. This inventive concept may, however, be embodied in many alternate forms and should not be construed as limited to the embodiments set forth herein.

Accordingly, while the inventive concept is susceptible to various modifications and alternative forms, specific embodiments thereof are shown by way of example in the drawings and will herein be described in detail. It should be understood, however, that there is no intent to limit the inventive concept to the particular forms disclosed, but on the contrary, the inventive concept is to cover all modifications, equivalents, and alternatives falling within the spirit and scope of the inventive concept as defined by the claims. Like numbers refer to like elements throughout the description of the figures.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises", "comprising," "includes" and/or "including" when used in this specification, specify the presence of stated features, integers, steps, operations, elements, and/or components, but do not preclude the presence or addition of one or more other features, integers, steps, operations, elements, components, and/or groups thereof. Moreover, when an element is referred to as being "responsive" or "connected" to another element, it can be directly responsive or connected to the other element, or intervening elements may be present. In contrast, when an element is referred to as being "directly responsive" or "directly connected" to another element, there are no intervening elements present. As used herein the term "and/or" includes any and all combinations of one or more of the associated listed items and may be abbreviated as "/".

Unless otherwise defined, all terms (including technical and scientific terms) used herein have the same meaning as commonly understood by one of ordinary skill in the art to which this inventive concept belongs. It will be further understood that terms used herein should be interpreted as having a meaning that is consistent with their meaning in the context of this specification and the relevant art and will not be interpreted in an idealized or overly formal sense unless expressly so defined herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element without departing from the teachings of the disclosure. Although some of the diagrams include arrows on communication paths to show a primary direction of communication, it is to be understood that communication may occur in the opposite direction to the depicted arrows.

Although many of the examples discussed herein refer to the sample being an eye and specific elements of an eye including the retina, cornea, anterior segment and lens of the eye, embodiments of the present inventive concept are not limited to this type of sample. Any type of sample that may be used in conjunction with embodiments discussed herein may be used without departing from the scope of the present inventive concept.

As discussed above, new techniques for accurate quantification of blood flows of both the retinal and uveal circulatory systems as an aid to improved diagnostics of diseases impacting the eye are desired. In particular, the human eye is nourished through two blood supplies: the uveal and the retinal circulatory systems. The choroid is part of the uveal blood supply in the eye, nourishing the outer and middle layers of the retina. Choriodal angiopathy is implicated in the major retinal diseases of children and adults. Retinopathy of Prematurity (ROP) is a critical threat to the premature infant, characterized by defects in vascularization associated with imbalanced oxygenation. Nearly 40,000 children are affected annually with ROP, and as the gestational age of viability decreases, the threat of life without sight is increasing.

Wet age-related macular degeneration (AMD) is associated with disruptions in Bruch's membrane at the choroid-retina barrier leading to abnormal vascularization and leakage originating in the outer retina. Over 1.75 million people in the United States have AMD with over 7 million at risk for developing AMD.

Diabetic retinopathy (DBR) is a risk to the 10 million diabetic patients worldwide. Proliferative DBR is associated with macular edema, vascular leakage, and disruptions in autoregulation.

Glaucoma affects 60 million patients world-wide, and is a complex disease that disrupts vascular autoregulation among its effects.

The choroid also plays an important role in myopia, and the uveal circulatory system that supports the outer structures of the eye from the posterior to the ciliary processes ties the structures that impact vision and accommodation.

Until recently clinical diagnostic tools have been limited to angiography of the retinal circulatory system, largely ignoring the role of the choroid. It is increasingly clear that changes to the morphology and function of the choroidal vasculature are important indicators of ocular health.

Figure 1B:
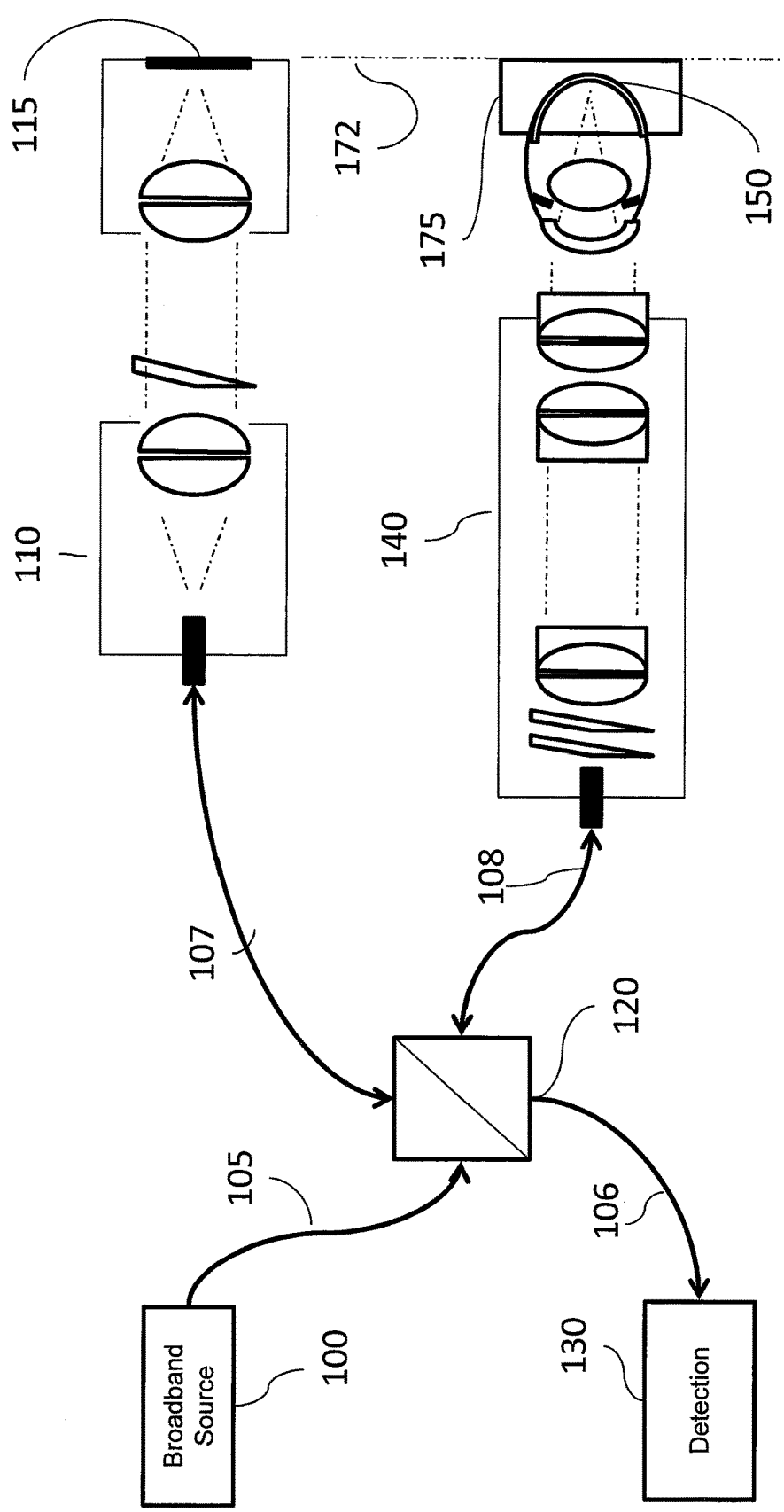
FIG. 1B is a block diagram illustrating an alternative Fourier domain Optical Coherence Tomography (FDOCT) system.

Current clinical implementations of retinal Fourier domain Optical Coherence Tomography (FDOCT) operate in the 800 nm waveband that has limited penetration into the choroid. Example FDOCT systems are illustrated in FIGS. 1A and 1B. Referring to FIGS. 1A and 1B, an FDOCT system includes a broadband source of optical radiation 100 transmitted along a source path 105 to an optical splitter/combiner 120, whereupon the optical radiation is directed along a reference path 107 to a reference reflector 110 and along a sample path 108 to an optical system 140 designed to image a scanning beam of optical radiation on to the retina 150 of a subject. Light returned from the reference reflector 110 is combined with light returned from the retina at the splitter combiner 120, and optically mixed radiation is directed along a detection path 106 towards a detection system 130 that detects the resultant spectrally dependent interferogram. A computer processor transforms the spectral interferogram into a spatial domain image using Fourier techniques.

The interferogram requires that the path optical path length from the splitter/combiner 120 to the reference reflector 110 match the optical path length to the retina 150, and that a spatial domain image is derived within a Fourier domain window 175 along an axial distance that is a function of the spectral sampling interval of the detection system 130, and that the axial optical resolution is a function of the bandwidth of the source 100. The Fourier processing of the spectral interferogram yields two mirror images of structures on either side of the path matching position 170. As such, the path matching position may be configured by controlling the reference arm path length to be interior to the retina, at position 170 in FIG. 1A, or may be positioned behind the retina, at position 172 of FIG. 1B. The derived images are nominally equivalent inversions of one another, but differ by mirror image artifacts that may fold back into the image of the primary subject matter, and by differences in the signal to noise ratio (SNR).

The path matching position 172 of FIG. 1B is sometimes desirable in visualization of the choroid because of improved signal to noise of the outer retina in this configuration. However, imaging into the choroid is fundamentally limited by retina pigmentation that inhibits photon penetration to the outer retina.

Referring now to FIGS. 2A through 2D, images of retinas of various ethnic groups will be discussed. Images of the retina of four different ethnic groups are illustrated in FIGS. 2A through 2D, Caucasian (2A); Indian (2B); African American (2C); and Semitic (2D). As illustrated, in each case, the outer retina is visible, but the boundary of the choroid with the sclera is not clearly differentiated.

In order to improve visualization of the choroid, using a longer wave light source at 1060 nm offers photon penetration advantages as the light scattering in tissue drops for longer wavelength ranges. Swept Source Optical Coherence Tomography (SS-OCT) operating at 1050 nm has been commercialized by Topcon (outside of U.S.) for increased penetration depth for retinal imaging. However, swept source technology remains prohibitively expensive and lacks the phase stability of spectral domain OCT. Until recently, the lack of an Indium Gallium Arsenide (InGaAs) linescan detector for use in long wave band has hindered the development of a Spectral Domain OCT (SDOCT) system at 1060 nm. An appropriately engineered SDOCT system may have certain advantages over SSOCT, including the reliability of passive components, high phase stability, and lower cost. High phase stability enables sensitive Doppler flow imaging, yielding a commercial OCT system with the benefits of extended depth imaging that provides both morphological and, perhaps more importantly, flow information in the choroid.

The chief barrier to clinical introduction of Doppler OCT is the difficulty in translating a Doppler phase shift to a reproducible, quantitative velocity or flow rate. There are three key barriers to accurate quantification of Doppler flow rates: vessel angle determination, achieving phase accuracy, and extending the range of accessible flow rates.

The velocity of flow in a sample may be computed from a measure of the phase shift observed in the backscatter of an interrogating beam, according to Eqn. 1:

$$v = \frac{f_D \cdot \lambda_0}{2 \cdot n \cdot \cos(\alpha)} = \frac{\Delta\phi \cdot \lambda_0}{4\pi \cdot T \cdot n \cdot \cos(\alpha)} = C \cdot \Delta\phi \cdot \left(\frac{1}{\cos(\alpha)}\right) \quad \text{(Eqn. 1)}$$

where v is velocity; $f_D$ is the Doppler frequency shift; $\Delta\phi$ is the measured phase shift; $\alpha$ is the angle of the vessel with respect to the interrogation beam; $\lambda_0$ is central wavelength of the OCT interrogation beam; T is sampling period; and n is refractive index. As is evidenced in Eqn. 1, the derived velocity (v), and precision and accuracy thereof, is dependent on the measured phase shift $\Delta\phi$ and the angle $\alpha$.

The relative error dv/v in a velocity measurement is associated with the relative error $d\alpha/\alpha$ in angle determination according to Eqn. 2 set out below.

$$\frac{dv}{v} = \alpha \cdot \tan(\alpha) \cdot \frac{d\alpha}{\alpha}$$

Figure 3:
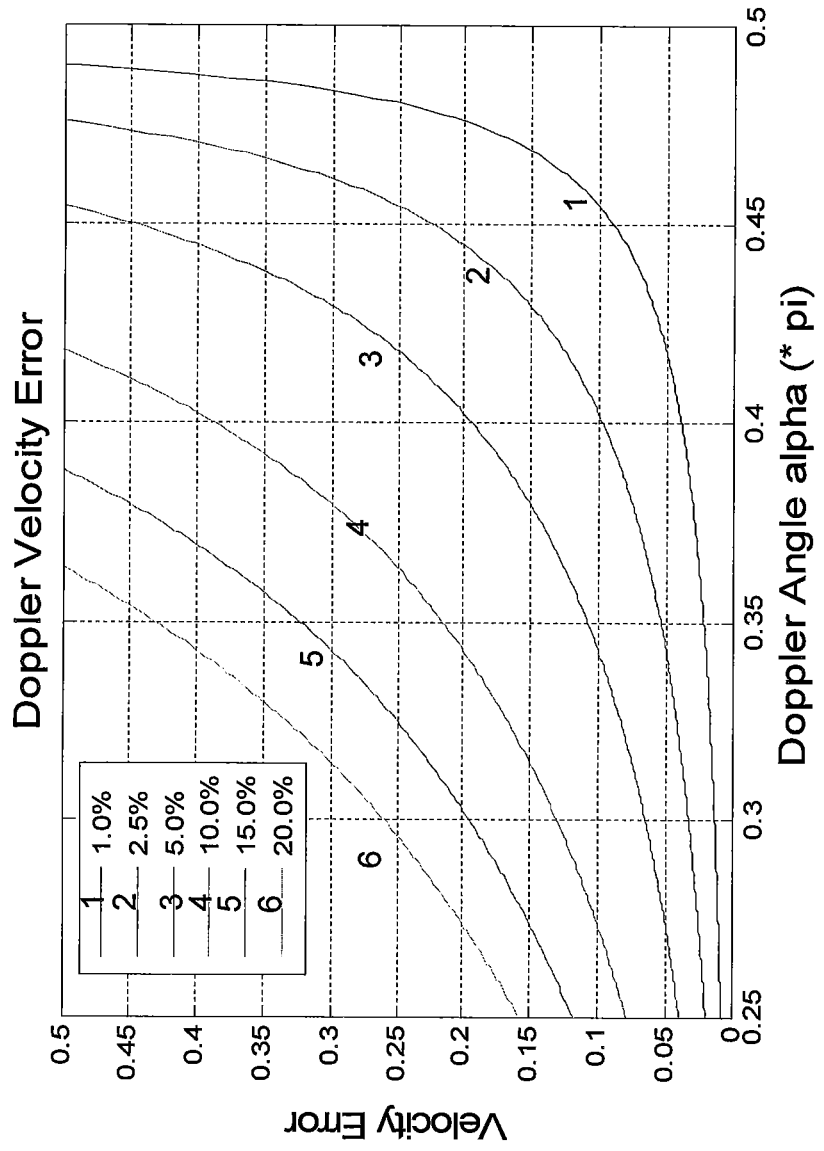
FIG. 3 is a graph illustrating doppler velocity error as a function of vessel angle and positional location error according to Eqn. 1, where v is velocity and a is flow angle relative to beam.

Eqn. 2 highlights the magnification of error as the direction of flow relative to the direction of interrogation a approaches 90 degrees as graphed in FIG. 3 as a function of angle error $d\alpha/\alpha$ (inset). In particular, the graph of FIG. 3 illustrates doppler velocity error (curves 1-6) as a function of vessel angle and positional location error according to Eqn. 1, where v is velocity and $\alpha$ is flow angle relative to beam. In biological imaging generally, and retinal imaging specifically, the angle $\alpha$ does generally approach 90 degrees. It is therefore important to reduce the error in angle determination to reduce the error in velocity determination to an acceptable level.

Figure 4:
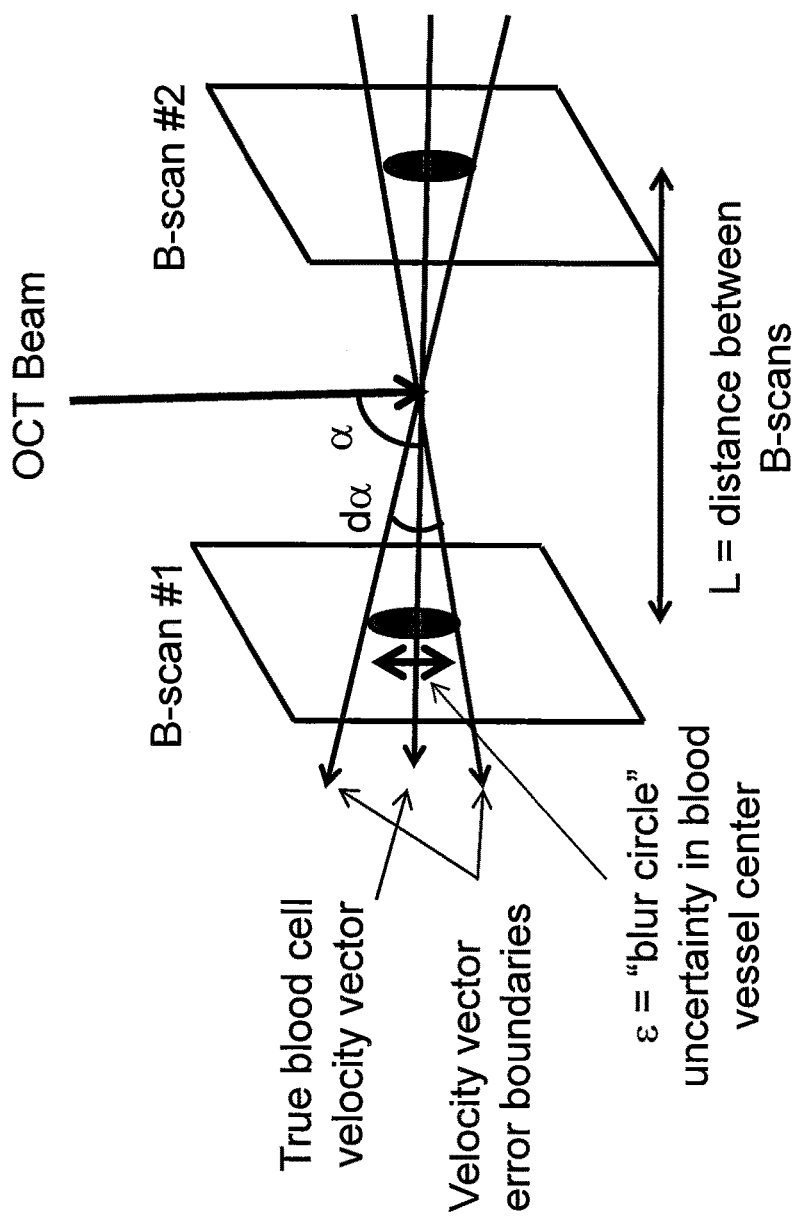
FIG. 4 is a block diagram illustrating first and second B-scans and various angles and distances related thereto in accordance with embodiment of the present inventive concept.

U.S. Pat. No. 8,244,334 to Huang discusses a two-scan angle estimation method, but is insufficient to reduce the angle estimation error. The error in a two-point estimation method is dependent on the error ε in estimating the position of the two points and the distance L between the two points as diagrammed in FIG. 4. In particular, as illustrated, the distance L represents the distance between OCT B-scans (B-scan #1 and B-scan #2) used to determine vessel locations. The combined error is computed from Eqn. 3 set out below and plotted in FIG. 5 (lines 1-6).

$$\frac{dv}{v} = 2 \cdot \sin^{-1}\left(\frac{\varepsilon}{L}\right) \cdot \tan(\alpha) \quad \text{(Eqn. 3)}$$

where ε is the "blur circle" uncertainty in blood vessel center (illustrated on FIG. 4); L is the distance between the two successive scans from which the angle is derived; and ε/L is the "blur ratio" important acquisition parameter.

Figure 5:
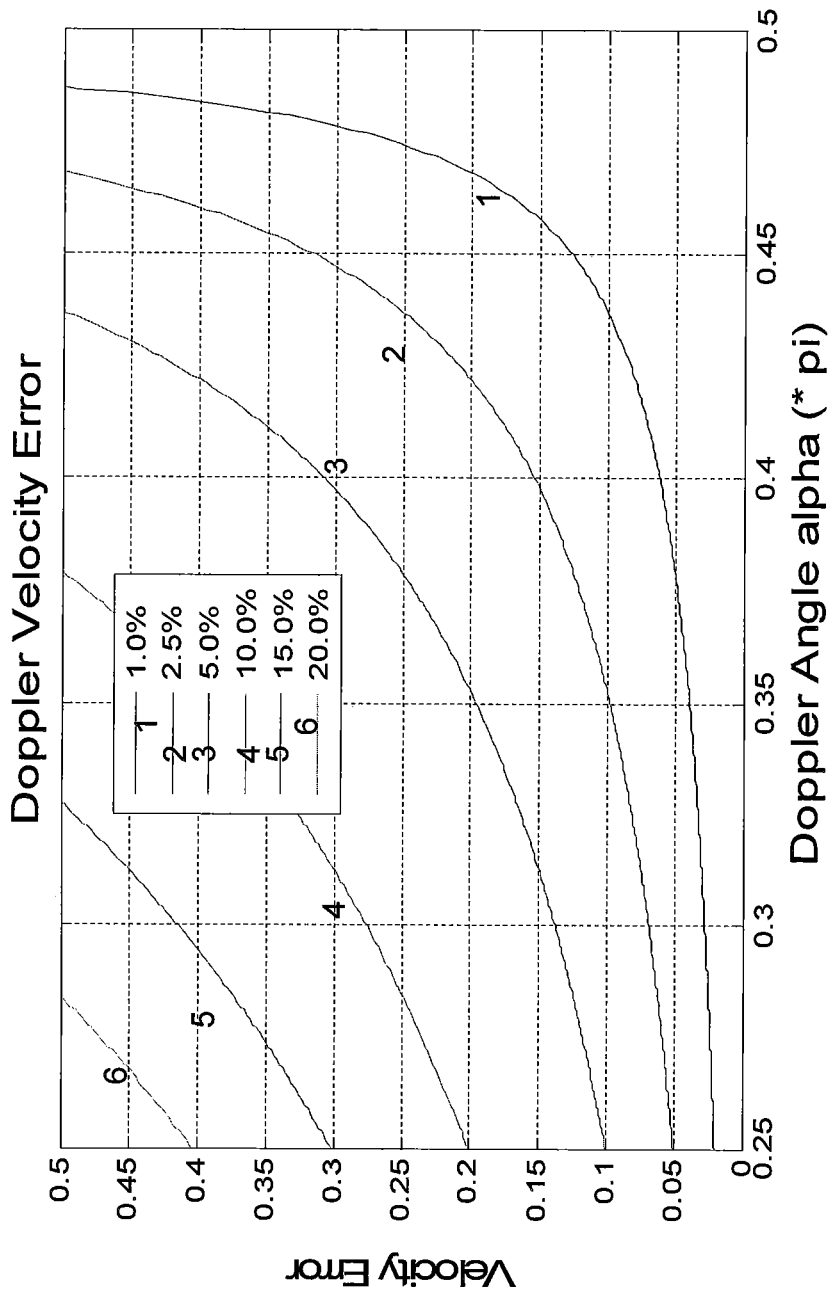
FIG. 5 is a graph illustrating doppler velocity error as a function of vessel angle and positional location error according to Eqn. 1, where v is velocity and $\alpha$ is flow angle relative to beam.

As is clear from the graphs illustrated in FIGS. 3 and 5, it is important to reduce the error in angle estimation. A two-point estimator is insufficient in practice.

In order to compute a flow angle, it is necessary to identify a position in space tied to the direction of flow that can be traced frame to frame, or B-scan to B-scan. One such method is to identify a centroid of flow within a vessel. The centroid may be found by one of multiple methods, including a hill-climb search, or a model-based smoothing or fit to the flow data, again taking advantage of known characteristics of vascular flow.

In order to derive a flow rate, determination of the cross section of the region or vessel of interest is required. An elliptical dimension may be derived using similar methods to the determination of centroid.

Figures 6A, 6B:
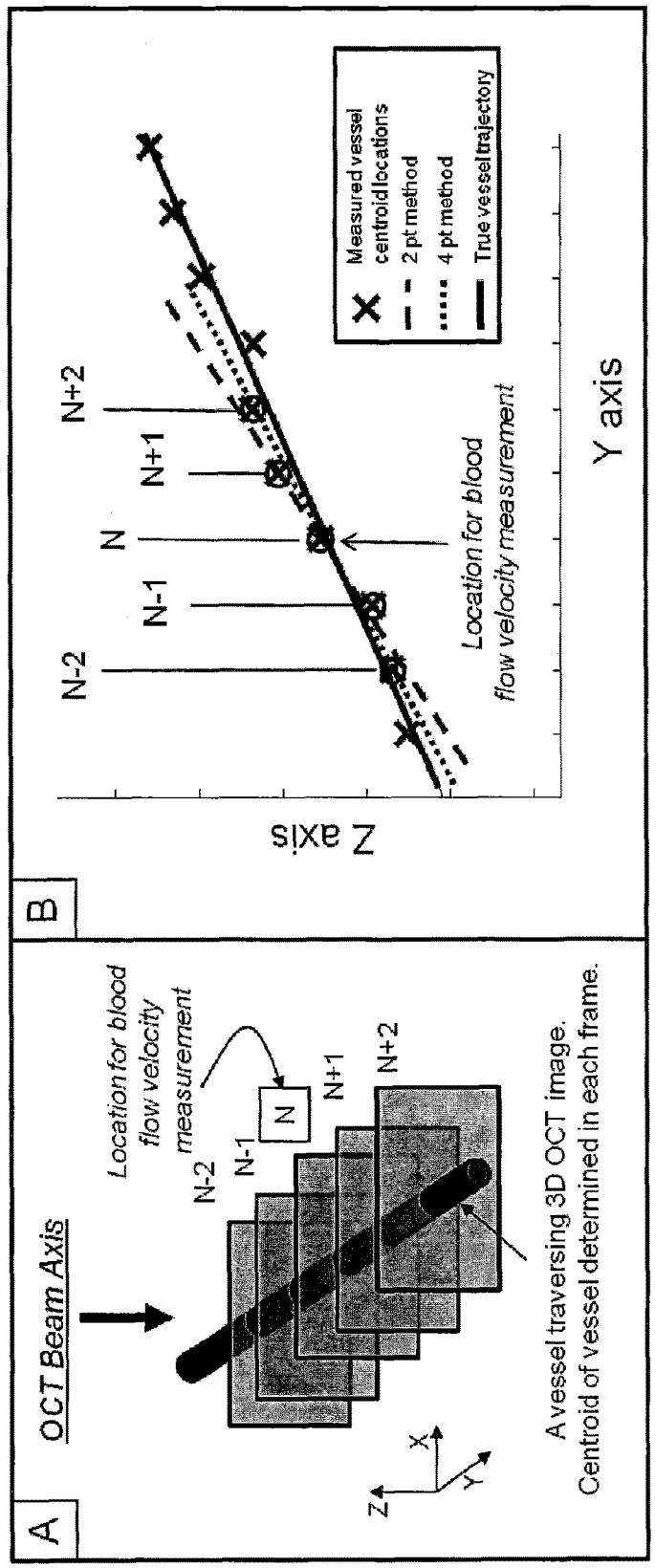
FIGS. 6A and 6B are block diagrams illustrating a multipoint method for determining vessel angle in accordance with some embodiments of the present inventive concept.
Figure 7:
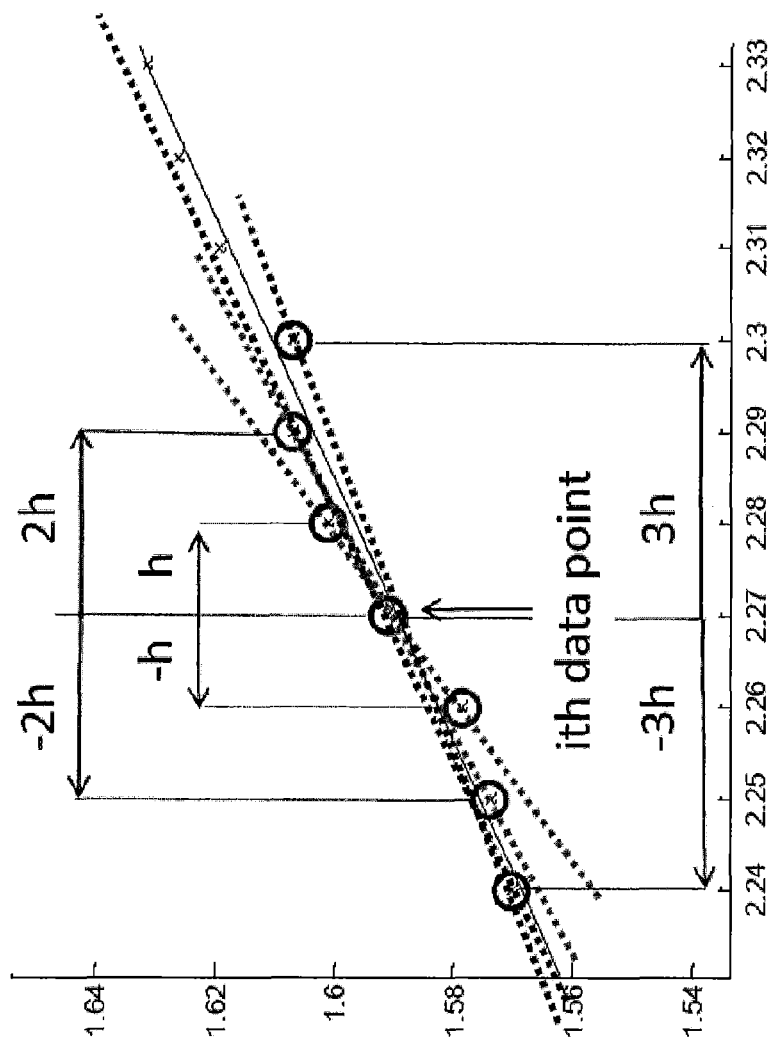
FIG. 7 is a diagram illustrating a multipoint method for determining vessel angle in accordance with some embodiments of the present inventive concept.

In some embodiments, an angle of flow may be computed by determining a spatial change across two or more B-scans. At a minimum, a change over two points may be used to identify an angle, but as has been discussed this is highly unlikely to yield accurate or reproducible results. Thus, some embodiments of the present inventive concept a multi-point slope estimator is applied to compute a slope in the presence of noisy data as illustrated in FIGS. 6A and 6B. In particular, FIGS. 6A and 6B illustrate a sampling strategy for computing vessel angle relative to OCT direction in accordance with some embodiments of the present inventive concept wherein axial position of the vessel is sampled at more than two points to improve the precision of angle determination In a three-point method, a slope at a central value is computed using values of reference point, such as flow centroid, at two neighboring positions as illustrated in FIG. 7, for example, a slope in B-scan_i is found computing the slope between B_scan_i−1 and B_scan_i+1. Similarly, in a five-point method, a slope at a central value is computed using values of reference point, such as flow centroid, at four neighboring positions, for example, a slope in B-scan_i is found computing the slope between B_scan_i−2 and B_scan_i+2 and between B_scan_i−1 and B_scan_i+1. In some embodiments, the average of the slope derived from nearest-neighbor points and the slope derived from the second-nearest-neighbor point may be taken and may improve the reproducibility of angle estimator over the two point method by approximately 74%. Other related methods of improving the accuracy of slope measurements using multi-point estimators may provide further improvement.

The distance between points used in the angle estimator impacts the accuracy and reproducibility. If the step size is too small, the error associated with centroid estimation magnifies the angle error, as in Eqn. 3. If the step size is too large vessel curvature may lead to inaccurate estimations. In some embodiments of the present inventive concept, the maximum step used in the angle estimation in retinal vasculature is 200 micrometers, and the minimum step used is between 10 micrometers, and may be 100 micrometers and 25 micrometers, respectively.

The range of detectable flow is bound on the slow end by the ability to resolve a motion induced phase shift above the noise floor, and on the fast end by the ability to recover cyclical two-pi ambiguities in the detected phase shift. In some embodiments of the inventive concept, phase unwrapping may be applied to extend the range of detectable velocities. In some embodiments, symmetry in the flow in lumens, such as blood vessels, may be used to improve the accuracy of phase unwrapping.

Phase unwrapping may be applied to a single region, or vessel of interest (VOI), or to a set of vessels without departing from the scope of the present inventive concept. One method for preparing data for phase unwrapping includes thresholding the denoised Doppler data set and excluding outliers from the denoised data set. Multiple methods may be applied to the exclusion of outliers, including a three-point method and a four-point method. In some cases, exclusion of outliers may not be necessary.

The phase unwrapping may be then accomplished using one or more of multiple methods, including a two-point method, a four-point method, or a model-based method. In the n-point methods, neighboring points are searched for sign-changes that represent phase wrap jumps. Use of multiple-points makes the discrimination of phase wraps less sensitive to residual noise but at the cost of spatial resolution.

Model-based phase unwrapping may be applied, for example, to blood vessels. Vascular flow is characterized by cylindrical symmetry and laminar boundary conditions. Flow velocity will be increasingly rapid towards the center of the vessel, allowing the application of search functions and decision functions that take advantage of these rather clear constraints to identify and correct phase wraps.

Phase accuracy is a function of the intrinsic phase stability of the imaging system, as well as the relative phase stability between the imaging system and the subject under test. Intrinsic phase stability furthermore is a function of the absolute physical stability of the system, as well as phase noise associated with the scatterers in motion within the sample. Physical stability is improved through the use of a passive imaging system, such as provided by a Spectral Domain OCT (SDOCT) system using passive optical paths and spectrometer. In the absence of an intrinsically stable system, a reference signal may be used, as proposed in U.S. Pat. No. 7,006,232 to Izatt et al. However such a system introduces additional complexity. A swept source may be used, but phase stability is generally reduced relative to an SDOCT system. Additionally, certain SDOCT systems use active spectrometer alignment systems that further introduce phase instability. Some embodiments of the present inventive concept use a maximally passive system with no parts moving (other than scanning mirrors) during an acquisition.

There remains phase noise associated with the detected signal. It is common to be interested in imaging flow in media with limited scattering in the direction of interrogation, including imaging of clear fluids and blood within biological systems. Averaging of the phase-dependent signal may be employed to reduce the intrinsic phase noise. In some embodiments of Doppler OCT, sequential depth-resolved A-scans are acquired at a fixed location in the sample, and phase change between these sequential A-scans is used to determine the Doppler phase shift. The level of noise is reduced by averaging the Doppler phase shift over an increasing multiple of A-scans. However, this increases the total acquisition time. In some embodiments of the present inventive concept the averaging may be optimized to optimize the relationship between phase noise and total imaging time.

Relative motion between the system and the subject under test is the next source of noise. Such relative motion occurs at multiple time scales. One time scale is a time that is a fraction of the time required to obtain a B-scan. A B-scan is an aggregation of A-scans that form a cross sectional image. Typically, a B-scan is on the order of 100 times to a few thousand times longer than an A-scan. In current generation OCT systems, the acquisition of a B-scan may take from about 1/1000 second to 1/10 second. Over such time frames, there may not be perceptible motion of the subject relative to the system, i.e. motion such that there is distortion in the structural image. But there is generally motion that is perceptible as a distortion in phase. In some embodiments of the present inventive concept, a bulk motion correction is applied to the phase representation of the image to correct the distortion caused by the motion.

In some embodiments, a collection of spectral domain A-scans are collected that form a spectral domain B-scan. The data is transformed into a complex spatial domain data set. Bulk motion correction is performed on the complex spatial domain data set. Following the bulk motion correction, a Doppler data set is computed. A multi-tiered data set is created that comprises the motion-corrected spatial domain data and the Doppler data, that may be presented in multiple ways, for example, in a data set of Doppler frequency shifts corresponding point-by-point with the spatial domain data set.

In some embodiments of the inventive concept information from the spatial domain data set may be combined with information from the Doppler data set to denoise the Doppler data set. As used herein, the term "denoise" refers to removing the noise from the image or scan.

In a typical image, multiple B-scans will be acquired to create either a volumetric image or a time-series image. The time for the total image acquisition may be from about 10 to about 100 times longer than a B-scan, sometimes longer. Over such time periods it is more common to have perceptible structural distortion between B-scans. In some embodiments of the inventive concept, a second class of bulk motion correction may be applied to the structural representation of the image.

Figure 8:
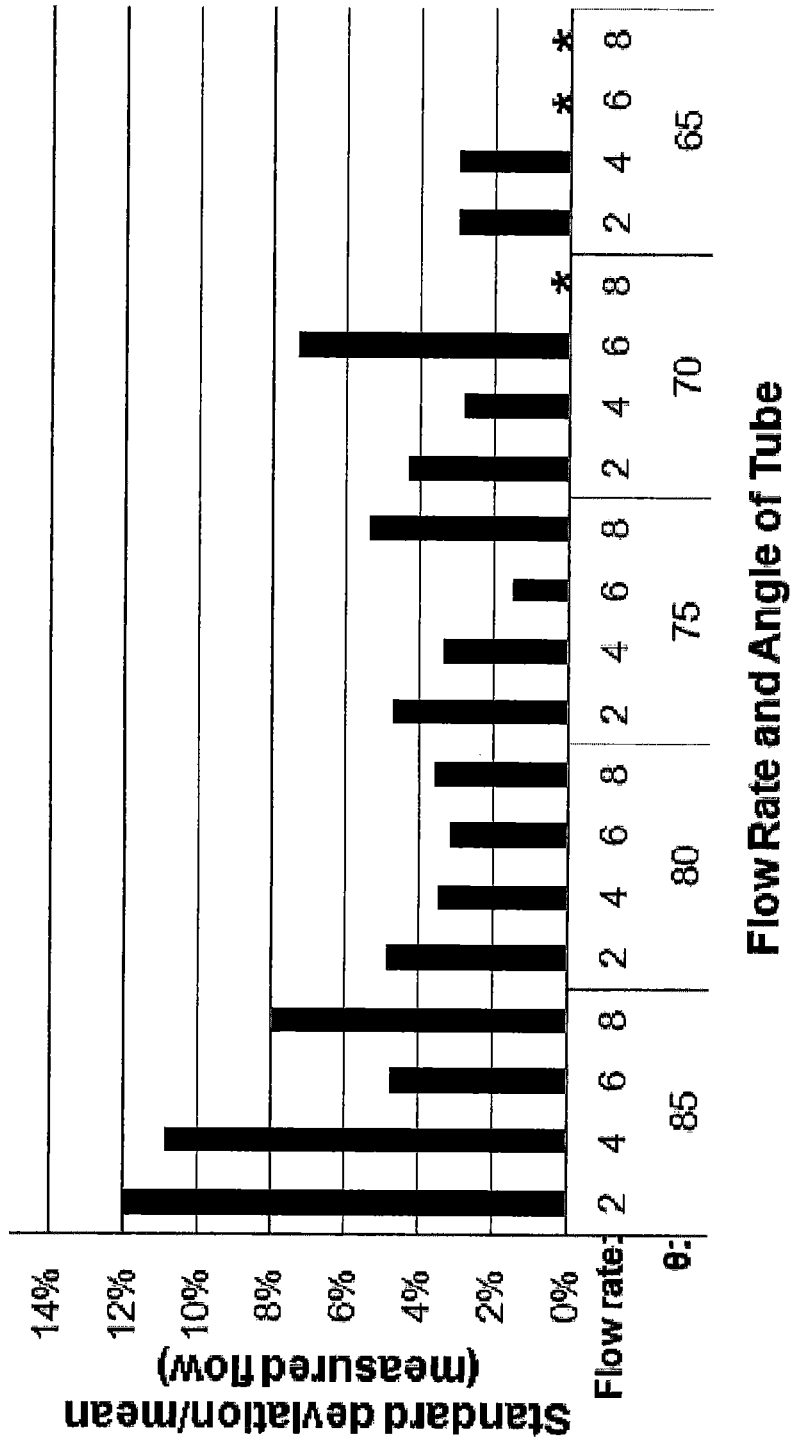
FIG. 8 is a graph illustrating measured flow rate precision as a function of flow rate and flow angle using Envisu C2300 Doppler imaging and flow phantom in accordance with embodiments of the present inventive concept.

Using a flow phantom, the reproducibility of computing Doppler flow rates as a function of flow rate and flow angle, with results shown in FIG. 8. As used herein, a "flow phantom" refers to a substitute or stand in that acts like a real "blood flow" for testing purposes. The flow phantom tested here comprises a tube through which fluid is pumped at a known rate, and interrogated with an OCT system at a known angle between the OCT beam and the tube flow. As illustrated, the reproducibility using our multi-point angle algorithm is 10% (standard deviation/mean).

Figure 9A:
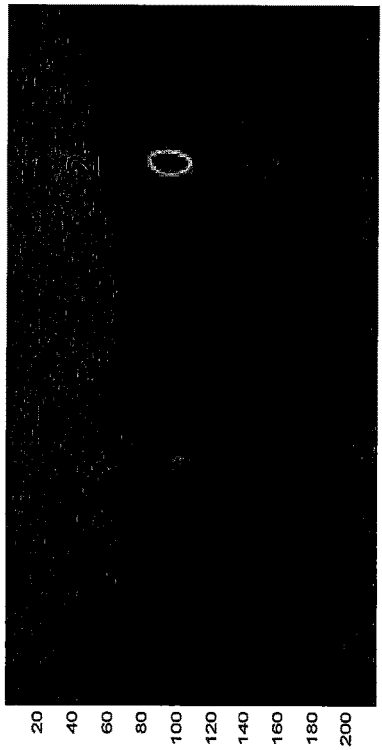
FIG. 9A illustrates a Doppler flow image with Vessels 1 and 2 produced in accordance with some embodiments of the preset inventive concept.
Figure 9B:
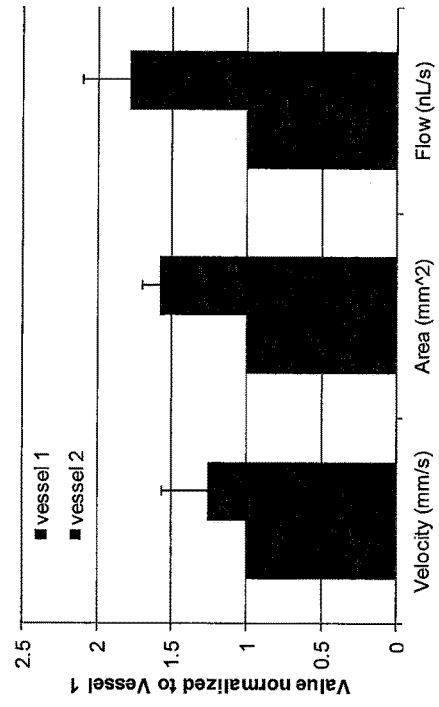
FIG. 9B illustrates normalized flow Vessels 1 and 2 indicating faster flow in 2 in accordance with some embodiments of the present inventive concept.
Figure 9C:
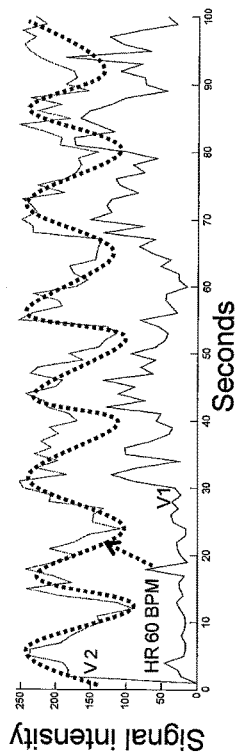
FIG. 9C illustrates flow as a function of time in Vessels 1 and 2 showing pulsality of flow in Vessel 2 in accordance with some embodiments of the present inventive concept.

FIGS. 9A, 9B and 9C are graphs illustrating the fundamental capability of Doppler processing in accordance with embodiments of the present inventive concept. In particular, FIG. 9A illustrated a phase-domain image of two vessels 1 and 2. FIG. 9B illustrates the associated velocities, vessel areas and flow rates. FIG. 9C illustrates the pulsatility of the arterial vessel (2) and the venous vessel (1).

Figures 10A, 10B:
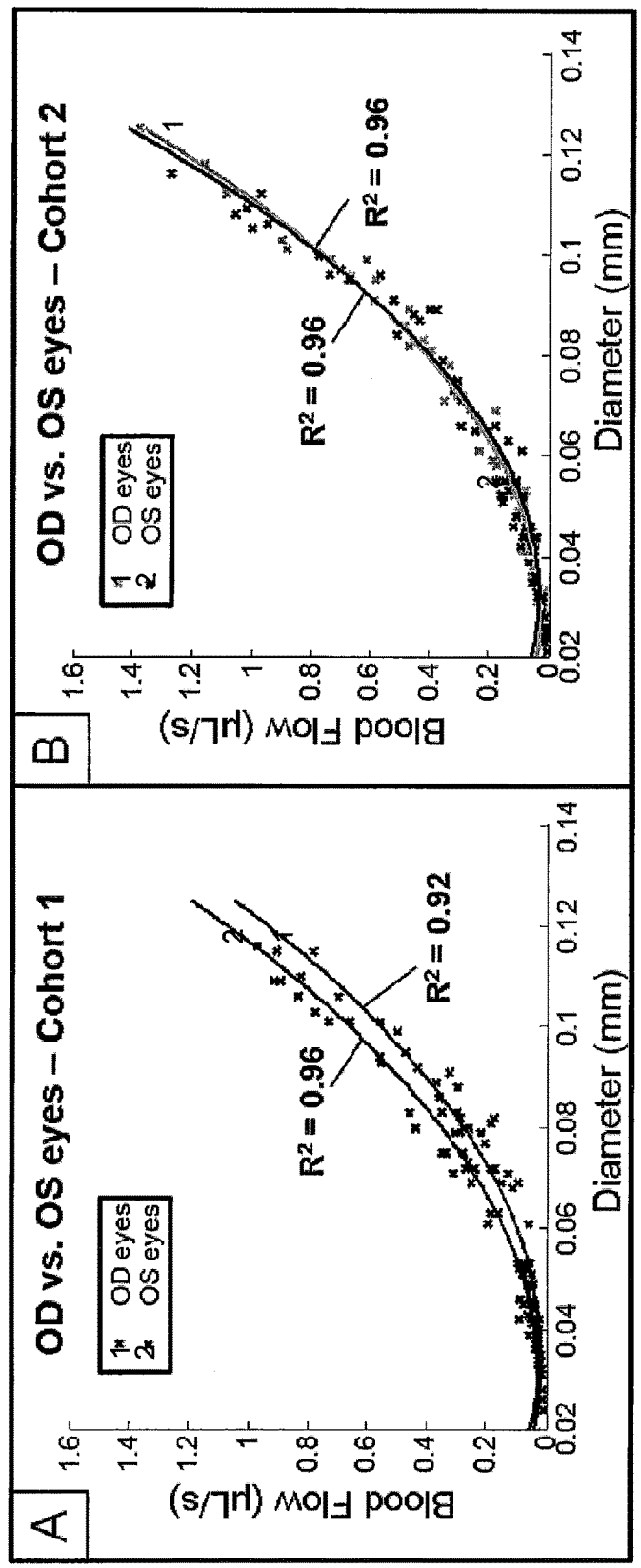
FIGS. 10A and 10B are graphs illustrating Results of a preliminary Doppler study on non-human primates using algorithms in accordance with some embodiments of the present inventive concept.

Referring now to FIGS. 10A and 10B, results of a preliminary Doppler study on non-human primates using algorithms in accordance with some embodiments of the present inventive concept will be discussed. In particular, the combination of techniques discussed herein has been applied to a preliminary trial on retinal vasculature on glaucomatous non-human primates. The key result is presented in FIGS. 10A and 10B. This result demonstrates an ability to differentiate among flows that vary by 20%, and that such a flow variation occurs at least in this glaucoma model. With this technique and robust, clinically-vetted hardware, the clinical utility of direct and differential (choroid and retina) Doppler OCT can be investigated. It will be understood that turbulent flow in the choroid may limit the power of phase unwrapping technique discussed herein and, thus, the maximum measurable choroidal flow.

In order to image and quantify flow in uveal, for example, choroidal, circulation, both an enhanced depth of 1060 nm and increased sampling rate are used. With 840 nm SDOCT operating at 36 kHz, the maximum velocity that can be measured (assuming a near-normal 85 degree angle of incidence) is 67 mm/s. In this ideal case, this is not likely to capture typical flow rates of 50-70 mm/s in the choroidal vessels before phase wrapping. With phase unwrapping, the measureable flow rate can be increased by a factor of at least 2 to 134 mm/s. Increasing the wavelength to 1060 nm increases the measureable flow rate 26% due to the wavelength-dependence of the Doppler flow signal and increasing the A-scan sampling rate by using a faster detection system will increase the measureable flow rate proportionately.

The dynamic range of relative phase measurements made in SDOCT is limited by the phase noise floor (on the low side) and phase washout (on the high side). The limited dynamic range of these phase measurements directly results in a limited dynamic range of flow velocities that can be measured.

Because phase measurements are periodic, phase wrapping can create ambiguity in velocity measurements if the velocity of the sample induces a phase shift greater than it between subsequent measurements. The velocity at which this occurs is given by Eqn. 4 set out below.

$$v_{wrap} = \frac{\lambda_0}{4nT\cos(\theta_D)} \quad \text{(Eqn. 4)}$$

where $\lambda_0$ is the center wavelength of the source; n is the index of the material; T is the inverse of the A-scan rate and $\theta_D$ is the Doppler angle between the velocity vector and the OCT beam.

Fringe washout refers to a condition in which phase shifts caused by the sample velocity result in OCT signal loss. This occurs because the amplitude of the interferometric fringe pattern oscillates during the integration time of the camera, resulting in a severe reduction in the measured fringe depth. The velocity at which this occurs is given by Eqn. 5 set out below.

$$v_{wash} = \frac{\lambda_0}{4n\tau\cos(\theta_D)} \quad \text{(Eqn. 5)}$$

where $\tau$ is the spectral integration time, i.e. the integration time of each spectral channel. In SDOCT, $\tau$=DT, where D is the camera duty cycle. As all of the spectral channels are acquired simultaneously and in parallel, $\tau$ is generally a large fraction of T.

In swept source (SS) OCT, spectral channels are acquired sequentially, rather than in parallel, and thus $\tau$=DT/M. Here, D is the duty cycle of the frequency swept laser and M is the number of spectral channels. As the number of spectral channels is typically on the order of ~1000, SSOCT has a ~1000× higher fringe washout velocity as compared to SDOCT. As phase stabilized SSOCT systems can have comparable phase stability to SDOCT systems, the minimum measurable phase shift (and thus the minimum measurable Doppler velocity) are approximately equal. Thus, in traditional implementations, SSOCT has approximately a 1000-fold larger Doppler velocity dynamic range as compared to SDOCT (assuming accurate phase unwrapping can be performed).

The Doppler dynamic range advantage that SSOCT has over SDOCT arises from the reduced spectral integration time $\tau$, because spectral channels are acquired sequentially rather than in parallel. However, the Doppler dynamic range of SDOCT could be dramatically improved if the duty cycle of the integration D were reduced.

In some embodiments, this can be achieved, without a loss in SNR, by modulating or switching the OCT light source while keeping the average power constant and also synchronizing the modulation or switching with the camera acquisitions. Potential embodiments of this technique include the use of direct diode current modulation, pulse-picking in pulsed or supercontinuum lasers, and optical shuttering using active optical modulators (acousto-optic or electro-optic), electro-optic switches, or high speed MEMS switches. It will be understood that embodiments of the present inventive concept are not limited to the examples provided herein.

As most commercial SDOCT systems use superluminescent diodes (SLDs) as the light source, in some embodiments the drive current of the SLD is directly modulated. Many SLDs can support modulation frequencies exceeding 100 MHz and, thus, can support the generation of pulses on the order of 10 ns. Such short pulses would confer to SDOCT a similar Doppler dynamic range as SSOCT. Special equipment required for this specific embodiment includes the SLD itself, appropriate electronic packaging (e.g. butterfly package), a diode current modulator (commercially available), and a function generator or digital to analog converter capable of generating the desired modulation waveform. All of these components are standard components in SDOCT systems, with the exception of the diode current modulator (which replaces a standard diode current controller).

In order to maintain signal quality and SNR, the average power must remain unchanged, which requires that the peak power increase by an amount proportional to the reduction in duty cycle. While this makes a 1000-fold increase in Doppler dynamic range impractical, improvements on the order of 10-fold can be achieved using a combination of techniques to increase the power incident on the sample, such as using a high powered SLD, overdriving the SLD, and/or modifying the coupler splitting ratio. Such a 10-fold improvement can confer an important advantage for clinical imaging, as it would enable the visualization of both very fast and very slow flow velocities. The juxtaposition of fast and slow flow rates is not uncommon, occurring, for example, in the optic disc where fast flowing arteries leading to the nerve head are located adjacent to capillary beds located within lamina cribrosa.

In further embodiments, a pulsed laser light source, such as a titanium sapphire (Ti:saph) or supercontinuum laser may be used. While these lasers typically have repetition rates on the order of tens of MHz, pulse-pickers (electro-optic or acousto-optic switches) can be used to select a subset of pulses. For example, a pulsed laser with a repetition rate of 100 MHz could be used in an OCT system operating at 100 kHz with a duty cycle of 10% (and 10-fold Doppler dynamic range improvement) by selecting the first 100 out of every 1000 pulses. These embodiments may simplify the task of directing sufficient power to the OCT system, as pulsed laser sources typically output abundant optical power. An ophthalmic OCT system operating at 840 nm with an 80/20 coupler typically requires about 5 mW of total source power to achieve the ANSI limited 700 µW maximum permissible exposure (MPE) incident on the patient's eye. Typical supercontinuum and Ti:saph lasers will output between 100 mW and 5 W, thereby supporting duty cycles between 20% and 0.1% and dynamic range improvements between 5× and 1000×, respectively.

In assessment of directionality of flow, Doppler OCT resolves directionality with respect to the interrogation beam, not with respect to the vector of flow. This can lead to further ambiguity and confusion, as a direction of flow along a plane perpendicular to the interrogation beam may be stable over a measurement area, but, as constrained within a lumen or blood vessel, may rise and fall along the axis of interrogation, providing a false sense of directionality or change in directionality. In some embodiments of the inventive concept, directionality along a plane of flow orthogonal to the direction of interrogation may be resolved.

In biological systems, such as the retina, blood flow is classified as arterial or venous, defining the in-flow and out-flow of blood to an organ. Arterial flow, typically, is pulsatile, and venous flow less so. It is frequently desirable to differentiate arterial and venous flow. In some embodiments of the inventive concept we differentiate between arterial and venous flow.

The pulsatility of flow presents another time scale to the measurement problem. Generally, the pulse rate is much slower than the A-scan rate, somewhat slower than the B-scan rate, and may be slower, faster or similar to the total acquisition rate. The problem encountered is that one does not generally know the position within a pulse cycle that a Doppler A-scan is acquired, meaning that the derived flow is a strong function of the time of interrogation within the cycle of pulsatilty. Furthermore, over a complete volume acquisition cycle, the flow will appear to fluctuate over space where the fluctuation is more properly viewed as fluctuation over time. In some embodiments of the inventive concept, the measurement of angle is separated from the measurement of time-dependent flow.

The contractility of vessels, as shown in FIG. 9C, presents another dimension that must be taken into account. Blood flow is due to the time course of the pulse cycle but may also be affected by the cross-sectional area of the vessel. Knowledge of the contractility of the vessel may provide additional information about the health of the vessel not provided by the blood flow data. In some embodiments of the inventive concept, the cross-sectional area is measured from structural information and this is coupled with the Doppler flow signal to provide information on the time dependence of contractility.

In some embodiments of an FDOCT imaging system or obtaining clinically relevant measures of both retinal and uveal flows, a 1060 nm SDOCT system is used, for example, the system illustrated in FIGS. 1A and/or 1B, designed around a spectrometer with 110 nm spectral bandwidth, an InGaAs line scan camera with 2048 pixels, and a 1070 nm SLD with 70 nm bandwidth, providing 5 mm imaging depth (in air) and 5 µm axial optical resolution operating at a 76,000 Hz readout rate. This provides resolution comparable to commercial 800 nm SDOCT systems with significantly improved image depth. In some embodiments, the optical fibers and couplers are replaced with Corning HI 1060 single mode optical fibers, and all bulk optics are optimized and coated for this wave band.

In some embodiment of the present inventive concept, a sampling and analysis strategy is used that allows for assessment of retinal and uveal flow rates by imaging target areas of the retina. Further clinical assessment may be provided by analyzing functional relationships between retinal and uveal flows and by analyzing functional relationships between changes in retinal and uveal flows as a function of time. Such function of time may incorporate, for example, disease progression, response to stimulus, response to therapy and the like. The functional relationship may be, for example, a simple algebraic difference between flow rates or flow volumes; simple algebraic ratios between flow rates or flow volumes; or more complex functional relationships that may further include differential measures of arterial and venous flows without departing from the scope of the present inventive concept. Stimuli may include changes in oxygenation or blood pressure or intraocular pressure. Therapies may be of any type of clinical intervention. It will be understood that the details herein are provided for example purposes only and should not be used to limit embodiments of the present inventive concept.

Figure 11:
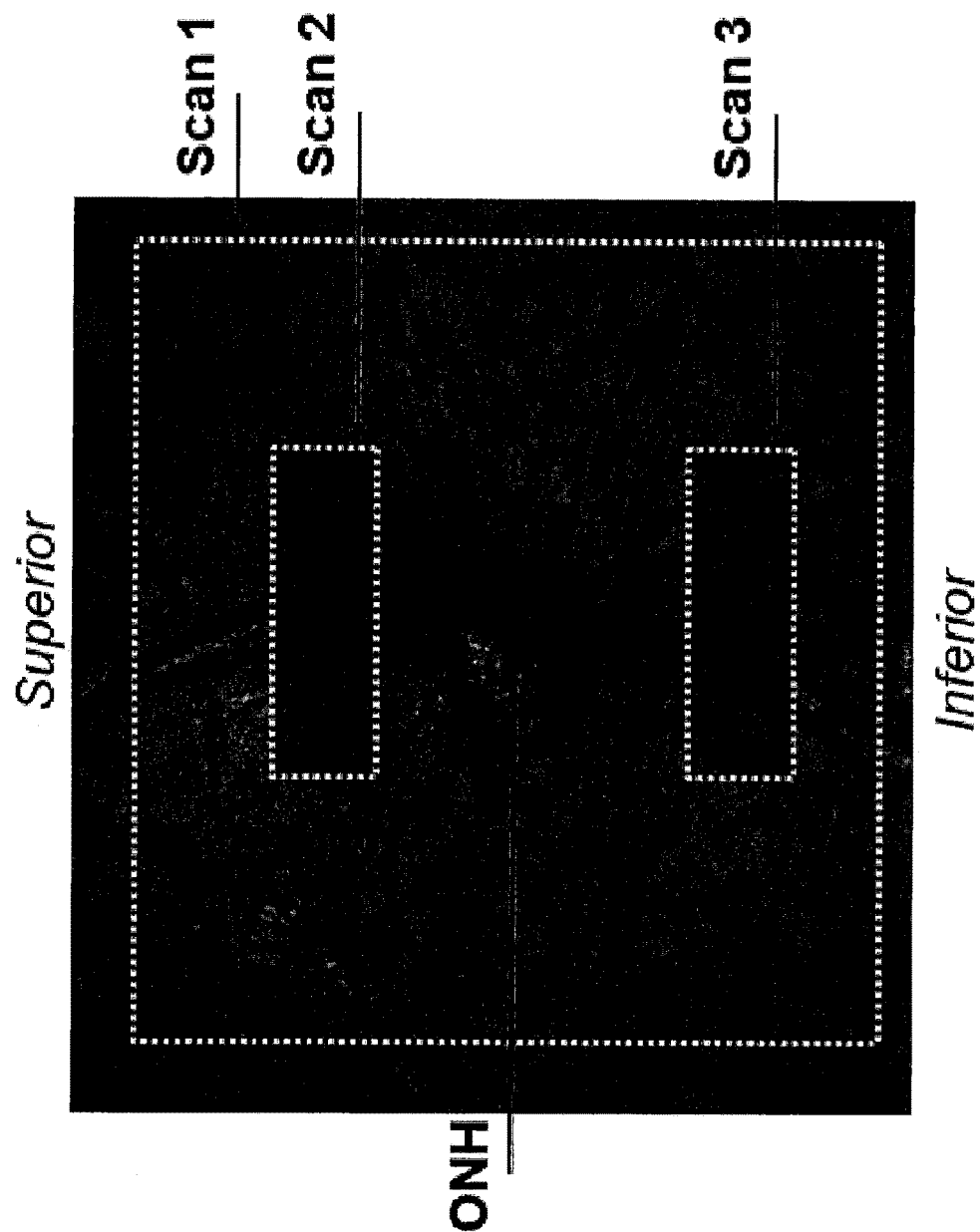
FIG. 11 is an image illustrating the sampling strategy in accordance with some embodiments of the present inventive concept.
Figure 12:
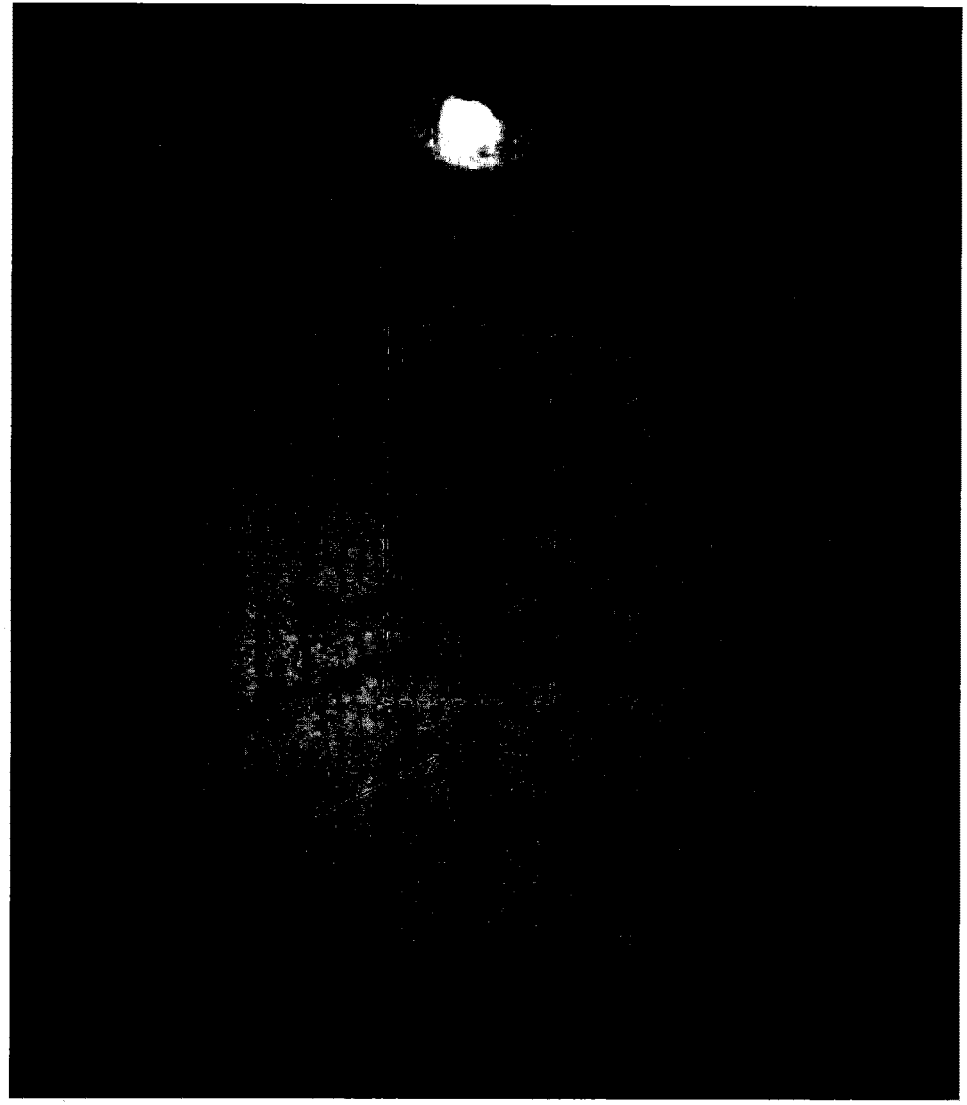
FIG. 12 is an image further illustrating the sampling strategy in accordance with some embodiments of the present inventive concept.

In some embodiments of the present inventive concept, a multi-step sampling strategy is used. Embodiments of the present inventive concept utilizing a multi-step sampling strategy will not be discussed. FIG. 11 is an image illustrating the sampling strategy in accordance with some embodiments of the present inventive concept. As illustrated 3 scans of an OCT en face image illustrating retinal vasculature are shown. Scan 1 is an isotropic wide field orientation scan and scans ⅔ are high density multi-frame vessel scans, superior and inferior, respectively. FIG. 12 is an image further illustrating the sampling strategy in accordance with some embodiments of the present inventive concept. In particular, FIG. 12 illustrates an OCT en face image of choroidal vasculature acquired with 860 nm Envisu C23000 in accordance with some embodiments of the present inventive concept. As shown in FIGS. 11 and 12, the patterns of retinal and choroidal vasculature are different, and a sampling strategy specific to these two circulatory systems is provided in accordance with embodiments of the present inventive concept.

Figure 13:
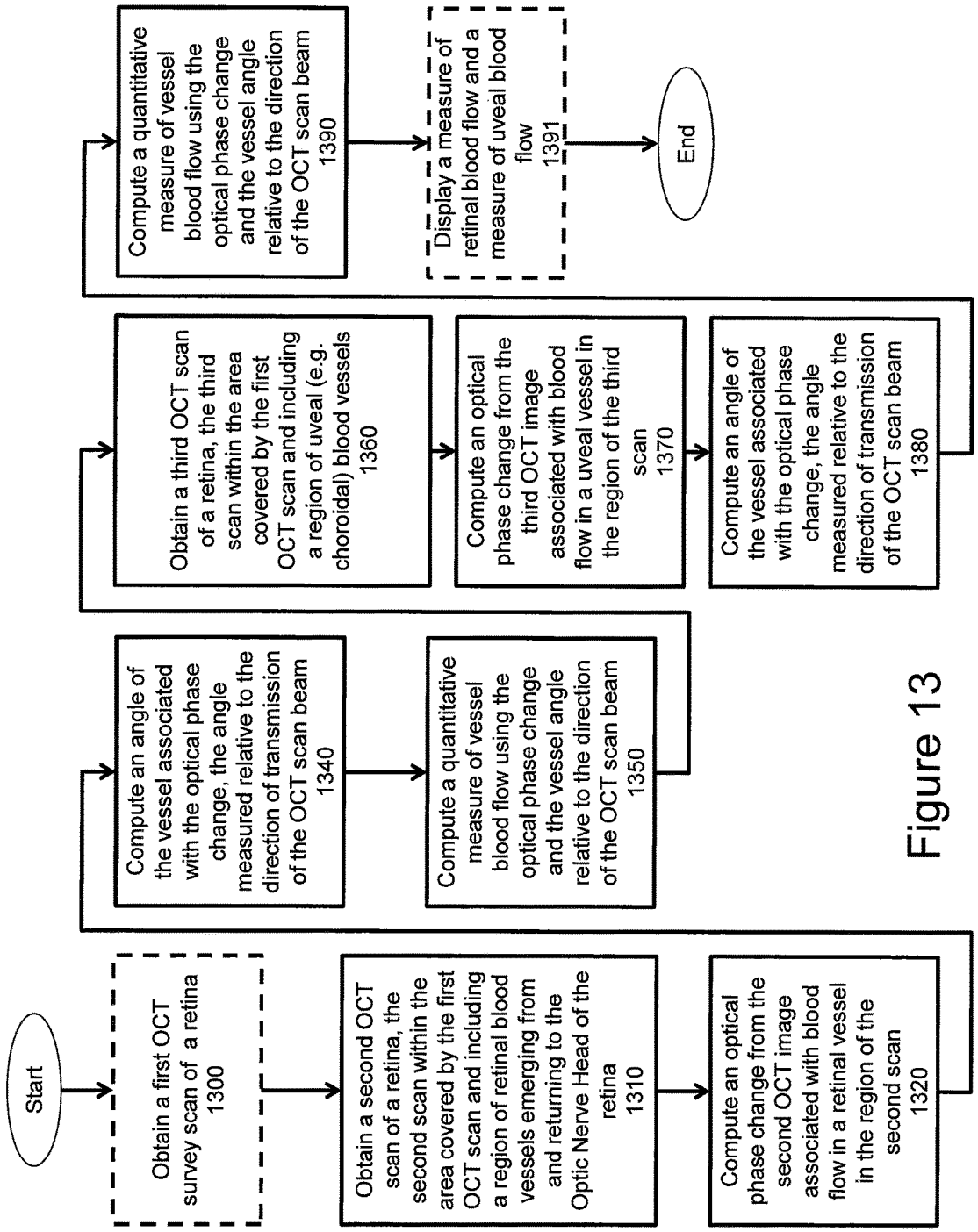
FIGS. 13 through 15 are flowcharts illustrating operations in accordance with various embodiments of the present inventive concept.

Referring now to the flowchart of FIG. 13, a first survey scan is acquired that curves a region of interest in the retina (block 1300). This survey scan provides an en face image against which the positions of subsequent scans are registered for positional reference. A second scan is acquired (block 1310) superior to, or inferior to, the optic nerve head, such that B-scans cut orthogonal to the major vascular arcades emanating from the optic nerve head. Three to seven spaced B-scans are spaced along the arcades, from which the vessel angles are determined. An additional series of B-scans may be acquired that sample the pulsatility of the arteries and allow for differentiation of the arteries and veins (blocks 1360-1380). The Doppler phase is computed (block 1320), the vessel angle is computed (block 1340), the vessel diameters (block 1350) may be computed, and flow rates and flow volumes may then be computed and displayed for the retinal flow (blocks 1390 and 1391).

As shown in FIG. 12, choroidal vessels are visible in the region between fovea and the optic nerve head, and between the arc of the major retinal arcades. Imaging the choroid in this region has the advantage of not being shadowed by light absorption and large flow rates of the primary retinal vessels. A similar sampling strategy is adopted for this region as describe above. The uveal circulatory of the outer retina includes relatively small vessels of the choriocapillaris as well as much larger vessels of the choroid. Doppler phases and vessel angles may be computed for any of these observed vessels, and flow rates and volumes computed.

Figure 14:
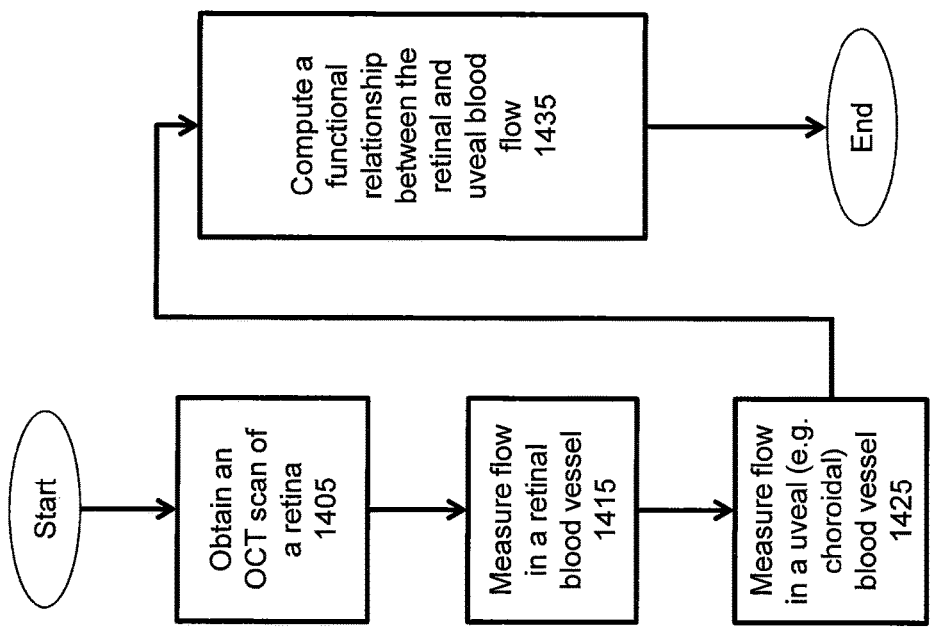

In some embodiments of the present inventive concept, clinical values are computed through a functional relationship between the retinal blood flows and the uveal blood flows, which will not be discussed with respect to FIG. 14. As illustrated in FIG. 14, operations begin at block 1405 by obtaining an OCT scan of a retina. The flow in a retinal blood vessel is measured (block 1415). Flow in the uveal, for example, choroidal, blood vessel is measured (block 1425). A functional relationship between the retinal and uveal blood flow is computed (block 1435). The functional relationship or relationships may further be relationships on flow rates or flow volumes or other values appropriately derived from motion-induced changes to the optical signal in an OCT measurement.

Figure 15:
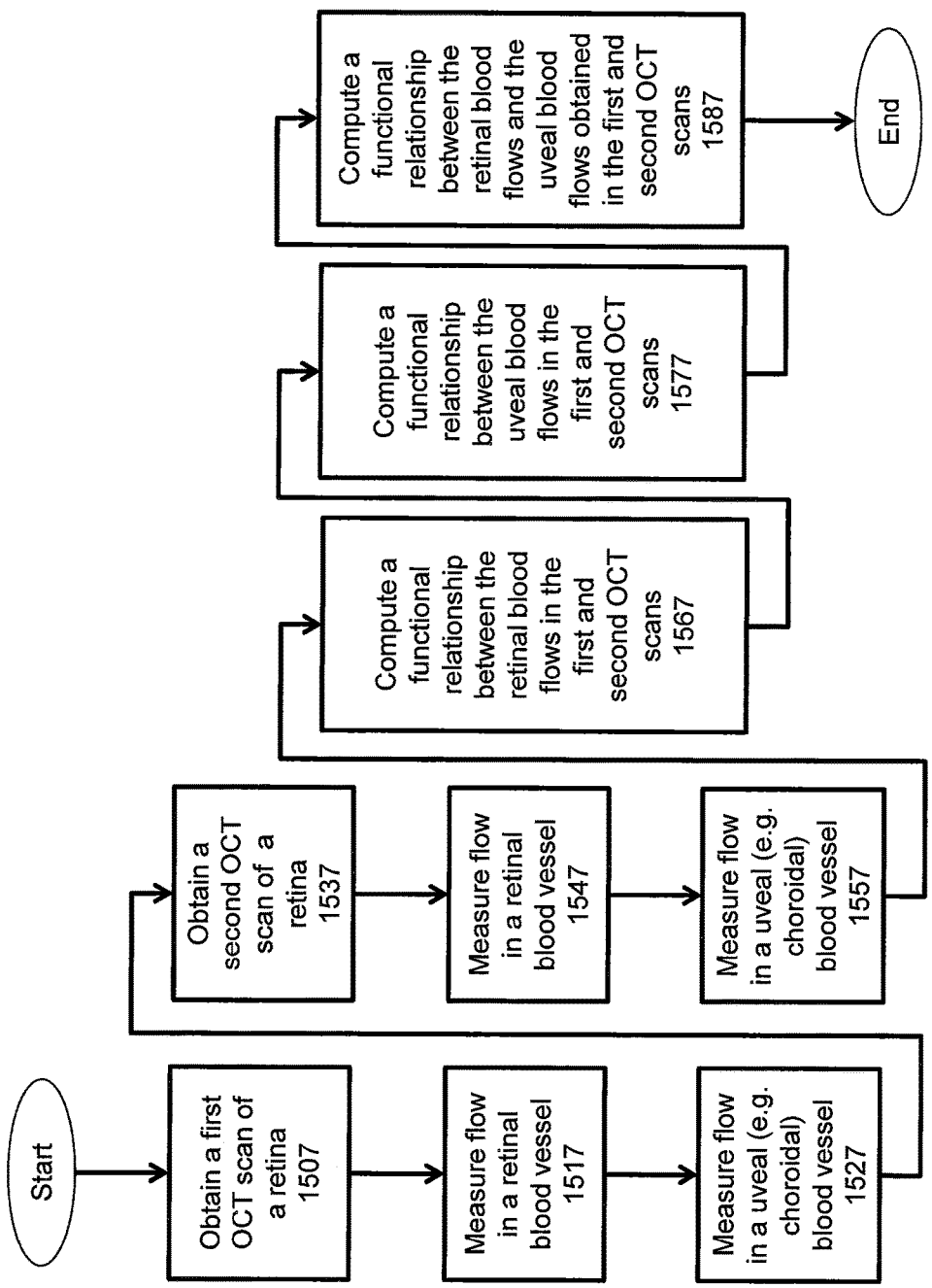

Referring now to the flowchart of FIG. 15, in some embodiments of the present inventive concept, clinical values may be computed through a functional relationship between changes in retinal and uveal blood flows, where the changes occur over time due to, for example, disease progression, influence of stimulus, or application of therapy. As illustrated in FIG. 15, operations begin at block 1507 by obtaining a first OCT scan of a retina. The flow in a retinal blood vessel is measured (block 1517). Flow in the uveal, for example, choroidal, blood vessel is measured (block 1527). A second OCT scan of a retina is obtained (block 1537). The flow in a second retinal blood vessel is measured (block 1547). Flow in the uveal, for example, choroidal, blood vessel is measured (block 1557). A functional relationship between the retinal blood flows in the first and second OCT scans may be computed (block 1567). A functional relationship between the uveal blood flows in the first and second OCT scans may be computed (block 1577). A functional relationship between the retinal blood flows and the uveal blood flows obtained in the first and second OCT scans may be computed (block 1587).

As briefly discussed above, embodiments of the present inventive concept maybe performed in an FDOCT system, for example, SDOCT or SSOCT system. Although the computational methods are discussed are based on OCT Doppler phase measurements, embodiments of the present inventive concept are not limited to this configuration and may be applied to other angiographic methods of OCT, such as phase variance and speckle variance techniques when those methods are used to derive quantitative information on flow. The clinical assessments discussed herein assume quantitative measures of flow in the retinal and uveal circulatory systems; qualitative representations of the relative flows in the two systems may be derived without specific quantification.

Figure 16:
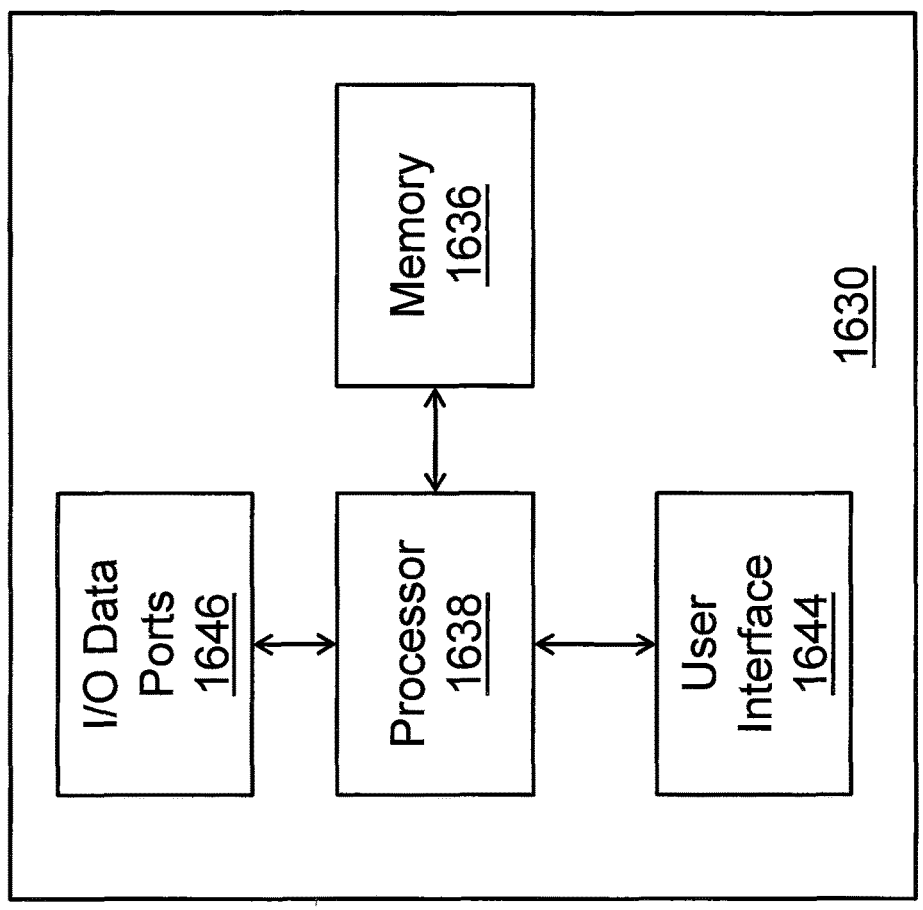
FIG. 16 is a block diagram of a data processing system that may be used in accordance with some embodiments of the present inventive concept.

As discussed above, some aspects of the present inventive concept may be implemented by a data processing system. Exemplary embodiments of a data processing system 1630 configured in accordance with embodiments of the present inventive concept will be discussed with respect to FIG. 16. As will be understood, the data processing system may be included in the OCT system of, for example, FIGS. 1A and 1B, or may be a separate device that communications with the system in FIGS. 1A and 1B without departing from the scope of the present inventive concept. The data processing system 1630 may include a user interface 1644, including, for example, input device(s) such as a keyboard or keypad, a display, a speaker and/or microphone, and a memory 1636 that communicate with a processor 1638. The data processing system 1630 may further include I/O data port(s) 1646 that also communicates with the processor 1638. The I/O data ports 1646 can be used to transfer information between the data processing system 1630 and another computer system or a network using, for example, an Internet Protocol (IP) connection. These components may be conventional components such as those used in many conventional data processing systems, which may be configured to operate as described herein.

Example embodiments are described above with reference to block diagrams and/or flowchart illustrations of methods, devices, systems and/or computer program products. It is understood that a block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means (functionality) and/or structure for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the functions/acts specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, example embodiments may be implemented in hardware and/or in software (including firmware, resident software, micro-code, etc.). Furthermore, example embodiments may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Computer program code for carrying out operations of data processing systems discussed herein may be written in a high-level programming language, such as Java, AJAX (Asynchronous JavaScript), C, and/or C++, for development convenience. In addition, computer program code for carrying out operations of example embodiments may also be written in other programming languages, such as, but not limited to, interpreted languages. Some modules or routines may be written in assembly language or even micro-code to enhance performance and/or memory usage. However, embodiments are not limited to a particular programming language. It will be further appreciated that the functionality of any or all of the program modules may also be implemented using discrete hardware components, one or more application specific integrated circuits (ASICs), or a field programmable gate array (FPGA), or a programmed digital signal processor, a programmed logic controller (PLC), or microcontroller.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated.

In the drawings and specification, there have been disclosed exemplary embodiments of the inventive concept. However, many variations and modifications can be made to these embodiments without substantially departing from the principles of the present inventive concept. Accordingly, although specific terms are used, they are used in a generic and descriptive sense only and not for purposes of limitation, the scope of the inventive concept being defined by the following claims.

That which is claimed is:

1. A method of obtaining a measure of blood flow using a Fourier domain optical coherence tomography (FDOCT) system, the method comprising:
    obtaining a first optical coherence tomography (OCT) survey scan of a retina of a subject using an OCT scan beam;
    obtaining a second OCT scan of the retina, the second OCT scan being within an area defined by the obtained first OCT scan and including a region of retinal blood vessels emerging from and returning to an Optic Nerve Head (ONH) of the retina;
    determining an optical phase change from the obtained second OCT scan, the optical phase change being associated with blood flow in a retinal blood vessel in the region of the second OCT scan;
    determining an angle of the retinal blood vessel associated with the optical phase change from the obtained second OCT scan, the angle being measured relative to a direction of transmission of the OCT scan beam of the obtained first OCT scan such that the angel is determined based on the first and second OCT scans; and
    computing a quantitative measure of vessel blood flow using the optical phase change from the obtained second OCT scan and the angle of the retinal blood vessel relative to the direction of the OCT scan beam of the obtained first scan such that the quantitative measure of vessel blood flow is product of the first and second OCT scans,
    wherein at least one of the steps of the method are performed by at least one processor.

2. The method of claim 1, further comprising:
    obtaining a third OCT scan of the retina, the third scan being within the area defined by the obtained first OCT scan and including a region of uveal blood vessels;
    determining a second optical phase change from the obtained third OCT scan associated with blood flow in a uveal vessel in the region of the third OCT scan;
    determining a second angle of a vessel associated with the second optical phase change from the obtained third OCT scan, the second angle measured relative to the direction of transmission of the OCT scan beam; and
    computing a quantitative measure of vessel blood flow using the second optical phase change and the second vessel angle relative to the direction of the OCT scan beam.

3. The method of claim 2, further comprising displaying at least one of a measure of retinal blood flow and a measure of uveal blood flow.

4. The method of claim 2, wherein the uveal region comprises a choroidal region.

5. The method of claim 1, wherein the FDOCT system comprises one of a spectral domain OCT system and a swept source OCT system.

6. The method of claim 1, wherein the first OCT survey scan comprises an en face image against which subsequent scans are registered for positional reference.

7. A method for computing clinical values using a Fourier domain optical coherence tomography (FDOCT) system, the method comprising:
    obtaining an OCT scan of a retina of a subject;
    measuring flow in a retinal blood vessel;
    measuring flow in a uveal blood vessel; and
    computing a functional relationship between the measured retinal and uveal blood flows,
    wherein at least one of the steps of the method are performed by at least one processor.

8. The method of claim 7, wherein a uveal region of the uveal blood vessel comprises a choroidal region.

9. The method of claim 7, wherein the FDOCT system comprises one of a spectral domain OCT system and a swept source OCT system.

10. A method for computing clinical values using a Fourier domain optical coherence tomography (FDOCT) system, the method comprising:
    obtaining a first OCT scan of a retina of a subject;
    measuring flow in a retinal blood vessel;
    measuring flow in a uveal blood vessel;
    obtaining a second OCT scan of the retina;
    measuring flow in a second retinal blood vessel;
    measuring flow in the uveal blood vessel; and
    computing a functional relationship between the measured retinal blood flows in the first and second OCT scans,
    wherein at least one of the steps of the method are performed by at least one processor.

11. The method of claim 10, further comprising computing a functional relationship between the measured uveal blood flows in the first and second OCT scans.

12. The method of claim 11, further comprising computing a functional relationship between the retinal blood flows and the uveal blood flows obtained in the first and second OCT scans.

13. The method of claim 12, wherein the functional relationships represent changes in retinal and uveal blood flows over time and wherein the changes in the retinal and uveal blood flows result from at least one of disease progression, influence of stimulus and or application of therapy.

14. The method of claim 10, wherein a uveal region including the uveal blood flows comprises a choroidal region.

15. The method of claim 10, wherein the FDOCT system comprises one of a spectral domain OCT system and a swept source OCT system.

16. A Fourier domain OCT (FDOCT) imaging system comprising:
    a source of broadband optical radiation;
    imaging optics to direct a scanning beam of optical radiation to a retina of a subject; and a processor configured to scan the beam of optical radiation in one or more defined patterns and derive separate measures of blood flow in retinal and uveal circulatory systems.

17. The system of claim 16, wherein the processor is further configured to:
   obtain a first optical coherence tomography (OCT) survey scan of the retina of the subject using an OCT scan beam;
   obtain a second OCT scan of the retina, the second OCT scan being within an area defined by the obtained first OCT scan and including a region of retinal blood vessels emerging from and returning to an Optic Nerve Head (ONH) of the retina;
   determine an optical phase change from the obtained second OCT scan, the optical phase change being associated with blood flow in a retinal blood vessel in the region of the second OCT scan;
   determine an angle of the retinal blood vessel associated with the optical phase change from the obtained second OCT scan, the angle being measured relative to a direction of transmission of the OCT scan beam of the obtained first OCT scan such that the angel is determined based on the first and second OCT scans; and
   compute a quantitative measure of vessel blood flow using the optical phase change from the obtained second OCT scan and the angle of the retinal blood vessel relative to the direction of the OCT scan beam of the obtained first scan such that the quantitative measure of vessel blood flow is product of the first and second OCT scans.

18. The system of claim 17, wherein the processor is further configured to:
   obtain a third OCT scan of the retina, the third scan being within the area defined by the obtained first OCT survey scan and including a region of uveal blood vessels;
   determine a second optical phase change from the obtained third OCT scan associated with blood flow in a uveal vessel in the region of the third OCT scan;
   determine a second angle of a vessel associated with the second optical phase change from the obtained third OCT scan, the second angle measured relative to the direction of transmission of the OCT scan beam; and
   compute a quantitative measure of vessel blood flow using the second optical phase change and the second vessel angle relative to the direction of the OCT scan beam.

19. The system of claim 18, wherein the processor is further configured to: display at least one of a measure of retinal blood flow and a measure of uveal blood flow.

20. The system of claim 16, wherein the processor is further configured to:
   obtain an OCT scan of a retina of a subject;
   measure flow in a retinal blood vessel;
   measure flow in a uveal blood vessel; and
   compute a functional relationship between the measured retinal and uveal blood flow.

21. The system of claim 16, wherein the processor is further configured to:
   obtain a first OCT scan of a retina of a subject;
   measure flow in a retinal blood vessel;
   measure f low in a uveal blood vessel;
   obtain a second OCT scan of the retina;
   measure flow in a second retinal blood vessel;
   measure flow in the uveal blood vessel; and
   compute a functional relationship between the measured retinal blood flows in the first and second OCT scans.

22. The system of claim 16, wherein the FDOCT system comprises one of a spectral domain OCT system and a swept source OCT system.

* * * * *

UNITED STATES PATENT AND TRADEMARK OFFICE
CERTIFICATE OF CORRECTION

PATENT NO. : 10,307,056 B2
APPLICATION NO. : 14/561684
DATED : June 4, 2019
INVENTOR(S) : Eric L. Buckland, Bradley A. Bower and Ryan Gessner It is certified that error appears in the above-identified patent and that said Letters Patent is hereby corrected as shown below:

In the Claims

Column 17, Line 46, change "angel" to -- angle --.

Column 19, Line 22, change "angel" to -- angle --.

Column 20, Line 27, change "f low" to -- flow --.

Signed and Sealed this
Ninth Day of July, 2019

Andrei Iancu
*Director of the United States Patent and Trademark Office*